(12) United States Patent
Damborsky et al.

(10) Patent No.: US 8,580,932 B2
(45) Date of Patent: Nov. 12, 2013

(54) METHOD OF THERMOSTABILIZATION OF A PROTEIN AND/OR STABILIZATION TOWARDS ORGANIC SOLVENTS

(75) Inventors: Jiri Damborsky, Brno (CZ); Zbynek Prokop, Brno (CZ); Tana Koudelakova, Brno (CZ); Veronika Stepankova, Slavkov u Brna (CZ); Radka Chaloupkova, Brno (CZ); Eva Chovancova, Tisnov (CZ); Artur Wiktor Gora, Bielsko-Biala (PL); Jan Brezovsky, Brno (CZ)

(73) Assignee: Masarykova Univerzita, Brno (CZ)

( * ) Notice: Subject to any disclaimer, the term of this patent is extended or adjusted under 35 U.S.C. 154(b) by 0 days.

(21) Appl. No.: 13/604,094

(22) Filed: Sep. 5, 2012

(65) Prior Publication Data

US 2013/0102763 A1    Apr. 25, 2013

(30) Foreign Application Priority Data

Oct. 25, 2011  (CZ) ................ PV-2011-680

(51) Int. Cl.
| | |
|---|---|
| *C07K 1/00* | (2006.01) |
| *C07K 14/00* | (2006.01) |
| *C07K 16/00* | (2006.01) |
| *C07K 17/00* | (2006.01) |
| *C08H 1/00* | (2006.01) |
| *A23J 1/00* | (2006.01) |
| *C07G 1/00* | (2011.01) |
| *C08H 7/00* | (2011.01) |
| *C08L 97/00* | (2006.01) |

(52) U.S. Cl.
USPC ............ 530/402; 530/427; 530/507

(58) Field of Classification Search
None
See application file for complete search history.

(56) References Cited

PUBLICATIONS

Miyazaki, K. and Arnold, F. Exploring nonnatural evolutionary pathways by saturation mutagenesis rapid improvement of protein function J Mol Evol (1999) 49:716-720.*
Anderson, D. et al. "Hydrophobic core repacking and aromatic aromatic interaction in the thermostable mutant of T4 lusozyme" Protein Science (1993) 2 1285-1290.*
Hao, J and Berry, A "A thermostable variant of fructose biphosphate aldolase constructed by directed evolution also shows increased stability in organic solvents" (2004) Protein Engineering, Design & Selection 17 689-697.*
Petrek, M. "CAVER: a new tool to explore routes from protein clefts, pockets and cavities" (2006) BMC Bioinformatics 316 1-9.*

* cited by examiner

*Primary Examiner* — John S Brusca
*Assistant Examiner* — Gerard LaCourciere
(74) *Attorney, Agent, or Firm* — Notaro, Michalos & Zaccaria P.C.

(57) ABSTRACT

Thermostabilization of a protein where the protein contains access routes and wherein at least one amino acid in the bottleneck of the access route is mutated, includes identifying the amino acids of the bottleneck and the amino acids control exchange of the solvent between a buried protein core and surrounding environment and/or in the packing of the amino acids inside the access route. Modification of the amino acids are determined so that the packing of the amino acids inside the tunnel is improved and the access route prevents access of undesired solvent molecules to the protein core, while allowing passage of the compounds necessary at the protein core to enable the protein to perform its biological function.

4 Claims, 8 Drawing Sheets
(8 of 8 Drawing Sheet(s) Filed in Color)

METHOD OF THERMOSTABILIZATION OF A PROTEIN AND/OR STABILIZATION TOWARDS ORGANIC SOLVENTS

FIELD OF THE INVENTION

The present invention relates to a method of modification of proteins which increases protein stability in organic solvents and protein thermostability.

BACKGROUND ART

Biotransformations represent an effective and sometimes preferable alternative to chemical synthesis for the production of fine chemicals and optically active compounds. The technological utility of enzymes can be enhanced greatly by using them at higher temperatures and in organic solvents rather than in aqueous reaction media. This is especially suitable for the modification of precursors of pharmaceutical compounds and fine chemicals, for which the enzymes do not show sufficient catalytic activities or which, in most cases, are insoluble or poorly soluble in water. However, the stability and activity of many enzymes is compromised at higher temperatures or in organic solvents. Prolonged enzyme activity in the presence of organic solvents is necessary to make such applications commercially successful. Therefore, several physical and chemical methods, such as immobilization, modification, and entrapment, for stabilizing enzymes in the presence of organic solvents were developed.

The use of enzymes in media-containing organic solvents significantly expands possibilities of their biotechnological applications (Klibanov, A. M. 2001: Improving enzymes by using them in organic solvents. Nature 409: 241-246). This approach is especially suitable for the modification of precursors of pharmaceutical compounds and fine chemicals, which, in most cases, are insoluble or poorly soluble in water (Carrea, G. and Riva, S. 2000: Properties and synthetic applications of enzymes in organic solvents. Angewandte Chemie International Edition 39: 2226-2254). Enzymatic selectivity, including substrate, stereo-, regio- and chemoselectivity, can be markedly affected, and sometimes even inverted, by the nature of the organic solvent used. Although water is the solvent of life, it is a poor solvent for most synthetic organic reactions. Thus, most chemists avoid aqueous solutions for synthetic applications. However, when removed from the aqueous environment and placed in an organic solvent, the activity of an enzyme is reduced greatly (Serdakowski, A. L. and Dordick, J. S. 2007: Enzyme activation for organic solvents made easy. Trends in Biotechnology 26: 48-54). Almost all naturally occurring enzymes are easily denatured and inactivated in the presence of organic solvents. Several physical and chemical methods for stabilizing enzymes in the presence of organic solvents, such as immobilization, surface modification and entrapment, were developed. Protein engineering using site directed mutagenesis and directed evolution are useful for clarifying why organic solvent-stable enzymes are stable in the presence of organic solvents and for developing organic solvent-stable mutant enzymes (Ogino, H. and Ishikawa, H. 2001: Enzymes which are stable in the presence of organic solvents. Journal of Bioscience and Bioengineering 91: 109-116; Gupta, A. and Khare, S. K. 2009: Enzymes from solvent-tolerant microbes: Useful biocatalysts for non-aqueous enzymology. Critical Reviews in Biotechnology 29: 44-54; Gupta M. N. and Roy, I. 2004: Enzymes in organic media. Forms, functions and applications. European Journal of Biochemistry 271: 2575-2583; Polizzi, K. M., Bommarius, A. S., Broering, J. M., Chaparro-Riggers, J. F. 2007: Stability of biocatalysts. Current Opinions in Chemical Biology 11: 220-225).

The most effective approach to a particular protein engineering task depends on the level to which the molecular basis for the desired property is understood or can be deduced from other proteins exhibiting that feature. Consistently successful "rational" or "semi-rational" design using site-directed mutagenesis or focused directed evolution to affect precise changes in amino acid sequence requires a high level of such understanding and useful strategy. An example of a generally applicable protein stabilization strategy is a metal ion chelation by specific surface dihistidine sites, which can affect the thermal stability as well as the protein's ability to withstand denaturants such as guanidinium chloride (Arnold, F. H. 1993: Engineering proteins for non-natural environments. The FASEB Journal 7: 744-749). Arnold and co-workers have contributed significantly to the application of the promising approach of protein engineering to improving enzyme function in organic solvents. Arnold has advocated a set of rules for protein design in non-aqueous solvents. The rules emphasized the importance of increasing conformational stability and compatibility of the enzyme surface with organic solvent (Arnold, F. H. 1993: Engineering proteins for non-natural environments. The FASEB Journal 7: 744-749; Gupta, M. N. 1992: Enzyme function in organic solvents. European Journal of Biochemistry 203: 25-32; Ogino H. and Ishikawa, H. 2001: Enzymes which are stable in the presence of organic solvents. Journal of Bioscience and Bioengineering 91: 109-116; Doukyu, N. and Ogino, H. 2010: Organic solvent-tolerant enzymes. Biochemical Engineering Journal 48: 270-282). Substitution of surface polar amino acids with hydrophobic amino acids was found to improve protein stability in organic solvents. It is believed that a more hydrophobic surface reduces the need for hydration required for maintaining native protein conformation (Gupta, M. N. 1992: Enzyme function in organic solvents. European Journal of Biochemistry 203: 25-32). Many proteins lose their biological activity via non-covalent processes (unfolding and subsequent aggregation) well before irreversible, covalent processes become important. Greater conformational stability can bring reduced rates of proteolysis and irreversible chemical degradation, as these processes often occur preferentially in unfolded proteins. As a result, an effective step toward engineering a protein that can tolerate unfavourable environments is to incorporate new stabilizing interactions to enhance its conformational stability and compensate for the interactions that were lost upon moving from the natural surroundings (Arnold, F. H. 1993: Engineering proteins for non-natural environments. The FASEB Journal 7: 744-749).

The shape of a protein is complicated by its many clefts, pockets, protrusions, channels and cavities. Protein concavities offer a unique microenvironment for biological functions, such as ligand binding or enzymatic catalysis. A large number of enzymes possess buried active sites that are connected to the external solvent environment by access routes (tunnels or channels). The character of the access routes may become an important determinant of enzyme substrate specificity (Petrek, M., Otyepka, M., Banas, P., Kosinova, P., Koca, J. and Damborsky, J. 2006: CAVER: a new tool to explore routes from protein clefts, pockets and cavities. BMC Bioinformatics 7: 316; Klvana, M., Pavlova, M., Koudelakova, T., Chaloupkova, R., Dvorak, P., Prokop, Z., Stsiapanava, A., Kuty, M., Kuta Smatanova, I., Dohnalek, J., Kulhanek, P., Wade, R. C., Damborsky, J. 2009: Pathways and mechanisms for product release in the engineered haloalkane dehalogenases explored using classical and random acceleration molecular dynamics simulations. Journal of Molecular Biology 392:

1339-1356). The accessibility of the access routes and the mechanisms of ligand exchange can be modified by mutations. The engineering of access pathways accessibility and the mechanisms of ligand exchange is a powerful strategy for modification of the functional properties of enzymes with buried active sites (Klvana, M., Pavlova, M., Koudelakova, T., Chaloupkova, R., Dvorak, P., Prokop, Z., Stsiapanava, A., Kuty, M., Kuta Smatanova, I., Dohnalek, J., Kulhanek, P., Wade, R. C., Damborsky, J. 2009: Pathways and mechanisms for product release in the engineered haloalkane dehalogenases explored using classical and random acceleration molecular dynamics simulations. Journal of Molecular Biology 392: 1339-1356). It has been shown that redesigning the amino acid residues in the access tunnels can prevent destabilization of the transition state by the water molecules and by this way increase the activity of an enzyme towards a specific substrate (Pavlova, M., Klvana, M., Prokop, Z., Chaloupkova, R., Banas, P., Otyepka, M., Wade, R. C., Tsuda, M., Nagata Y., Damborsky, J. 2009: Redesigning dehalogenase access tunnels as a strategy for degrading an anthropogenic substrate. Nature Chemical Biology 5: 727-733). All the publications dealing so far with the modification of access routes suggest this modification for improvement or modification of enzyme activity or selectivity, and therefore they concentrate on modification of residues that are involved in binding substrate, stabilization of transition states and in directing the substrates into the active site and the products out of the active site.

The present invention provides a method for modification of the access routes in order to achieve a greater stability of the protein towards solvents as well as a greater thermostability.

DISCLOSURE OF THE INVENTION

The present invention provides a method of stabilization of proteins towards organic solvents and/or thermostabilization of proteins based on rational design strategies, wherein at least one amino acid in the bottleneck of the access route of the protein is mutated.

A thermostabilization means stabilization in a temperature which is higher than the temperature in which the protein occurs in its natural environment.

An "access route" connects the core of the protein with the surrounding environment. Often, the access route is the pathway, by which the molecules necessary for the protein to perform its biological function, such as substrates, products, solvents and/or ions, access and leave the buried functionally-important sites. A "channel" is a pathway leading through the protein structure—both sides of the channel are open to the surrounding solvent. A "tunnel" is a pathway connecting a space buried in the protein core with the surrounding solvent—one side of the tunnel terminates in the protein structure, while the other side is open to the solvent. The term "access route" includes both the channels and the tunnels. A "bottleneck" is the narrowest point of an access route.

In this new approach, the redesigning of the bottlenecks of the access routes leads to an effective and selective discrimination between the molecules of a substrate/product and the destabilizing organic solvent molecules in the access routes, i.e., in channels and/or tunnels. At the same time, the introduced mutations improve the packing of the protein hydrophobic core resulting in an enhanced thermostability.

Many proteins act as enzymes, their core contains an active site and their biological function is a catalytic function. The stabilization of enzymes towards organic solvents and/or their thermostabilization is very important for many industrial processes using enzymatic catalysis. Therefore, in one preferred embodiment of the present invention, the protein is an enzyme.

The method of stabilization of proteins according to the present invention includes the following steps:

a) identification of the amino acids to be modified. The present method is based on the modification of the amino acids forming the bottlenecks of the access routes, thus in this step the amino acids defining the narrowest points of the access routes, so called bottlenecks, are identified in a protein with a known 3D structure. Selected amino acid residues should form the narrowest point of the wall of a protein tunnel or channel, participate in packing of the residues inside this tunnel or channel and/or determine the exchange of the solvent between the buried functionally-important site and the surrounding environment. The residues lining the access routes and forming the bottlenecks can be found using, e.g., freely available software Hotspot Wizard (Pavelka, A., Chovancova, E., a Damborsky, J. 2009: HotSpot Wizard: a web server for identification of hot spots in protein engineering. Nucleic Acids Research 37: W376-383), CAVER software (Petrek, M., Otyepka, M., Banas, P., Kosinova, P., Koca, J., and Damborsky, J. 2006: CAVER: a new tool to explore routes from protein clefts, pockets and cavities, BMC Bioinformatics 7: 316) or FoldX software (Guerois, R., Nielsen, J. E., and Serrano, L. 2002: Predicting changes in the stability of proteins and protein complexes: a study of more than 1000 mutations. Journal of Molecular Biology 320: 369-387).

b) modification of the amino acids determined in the step a) so that the packing of the amino acids inside the access route is improved and the new anatomy of the bottlenecks prevents the access of the undesired solvent molecules to the protein core, while it allows the passage of the compounds necessary at the protein core to enable the protein to perform its biological function(s). The amino acid substitutions must be selected according to the required size and physico-chemical properties and introduced using site-directed mutagenesis or other suitable methods known in the art. The selection of the modifying amino acids and the optimization can be carried out using methods known in the art, such as directed evolution using widely available commercial kits. The amino acids closing the access route for undesired molecules, yet allowing the passage of the compounds necessary at the protein core to enable the protein to perform its biological function(s), such as substrates, products, ions, solvents, etc., must be introduced. Especially amino acids with side-chains possessing two states (open and closed) and thus creating a so called molecular gate can result in both good stability and retained functionality. The aromatic residues, such as phenylalanine (Phe), tyrosine (Tyr) or tryptophan (Trp), enabling the aromatic stacking interactions are particularly suitable for this purpose, all three of them being among the most abundant gating residues in the natural proteins. Whenever it is uncertain, which amino acids will improve protein stability and retain the activity, saturation mutagenesis should be applied using the directed evolution techniques known in the art.

c) optionally assessment of the result of the modification. The mutagenesis of the residues located in the access tunnel is followed by the expression and screening of the thus created individual mutants or mutant library. During the expression step the mutated genes are transformed into the selected host expression system and the corresponding protein is synthesized. The protein is analyzed either in the form of whole cells containing the expressed protein, crude extract, partially purified or purified protein. The screening includes applying an assay for the visualization of the protein function (e.g., colorimetric assay, pH assay, gas chromatography, mass spectrometry, isothermal titration calorimetry) or the protein structural stability (e.g., circular dichroism spectroscopy, fluorescence spectroscopy, differential scanning calorimetry, NMR) in the presence of an organic solvent or at an elevated temperature. The thermal stability of a protein is well characterised by the melting temperature, which is the temperature when half of the protein is unfolded and half remains in its native form. The melting temperature is evaluated by monitoring the structural changes via a physical method (e.g., circular dichroism spectroscopy, fluorescence spectroscopy, differential scanning calorimetry, activity) at an increased temperature. Kinetic stability is measured as the residual activity in the presence of organic solvent or at an elevated temperature in time. The mutants with the respective improved property are selected from the candidates or mutant library based on the results of the assessment (activity or structural stability). If a further improvement is needed, the chosen candidates are used as templates for a further round of mutagenesis (step b). For tunnel residues, stabilization effects of all possible single-point mutations may be estimated in silico using the algorithm implemented in the FoldX <Build-Model> module (Guerois, R., Nielsen, J. E., and Serrano, L. 2002: Predicting changes in the stability of proteins and protein complexes: a study of more than 1000 mutations. Journal of Molecular Biology 320: 369-387).

Current methods of protein engineering either mutate any possible amino acid in the engineered protein (method of random mutagenesis) or target selected parts of the protein (the method of site-directed mutagenesis). The first approach generates an enormously large library of constructs in which most changes do not bring any positive effect on the property being developed. The testing of such libraries is time consuming and very costly. The targeted protein engineering using rationally focused specific mutations (that mutate only a limited number of selected amino acids) thus reduce the intensity of mutagenesis and the subsequent testing of the library and significantly increase the proportion of the positive mutations in the created library. However, the rational focused mutagenesis requires a detailed knowledge of which amino acid residues can affect the engineered property of the protein, in general this means that it is necessary to know the whole structure of the protein.

The newly proposed method of the present invention, unlike other methods of directed mutagenesis, targets specifically only the amino acids in the bottlenecks of the access routes of a protein. The amino acids forming the bottlenecks of these routes are the suitable sites for mutagenesis. The advantage of this method is that it leads to a small number of constructs. The thermal stability of the protein is increased due to the strengthening of hydrophobic interactions within the protein structure. The resistance to organic solvents is ensured by selective dismissals of molecules of substrate/product in/out of protein and retention of organic solvent molecules outside the protein interior. Modification of protein channel and tunnel bottlenecks leads to the protein's ability to selectively discriminate between the substrate/product/solvent/ion and the undesired solvent molecules and leads to improved packing of the amino acids inside the access route to stabilize the protein in the presence of the organic solvent and towards increased temperatures.

BRIEF DESCRIPTION OF DRAWINGS

The patent application file contains at least one drawing executed in color. Copies of this patent or patent application publication with color drawings will be provided by the Office upon request and payment of the necessary fee.

EXAMPLES OF CARRYING OUT THE INVENTION

Example 1

Figure 1:
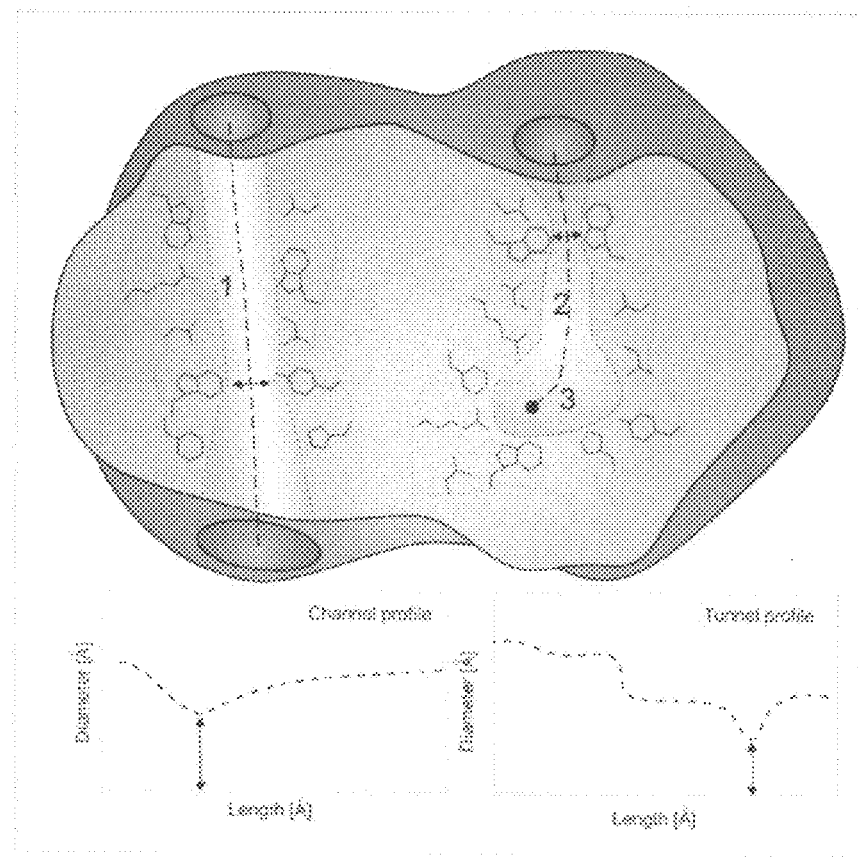
FIG. 1. Schematic representation of a protein with a channel (1), a tunnel (2), and a cavity (3). Voids interior is in bright colour, entrance in dark colour, channel- and tunnel-lining residues are in black, bottleneck residues are in red, arrows indicate bottleneck, groove channel and tunnel profile on bottom correspond to the dashed line, black dot corresponds to the starting point of tunnel profile.
Figure 2:
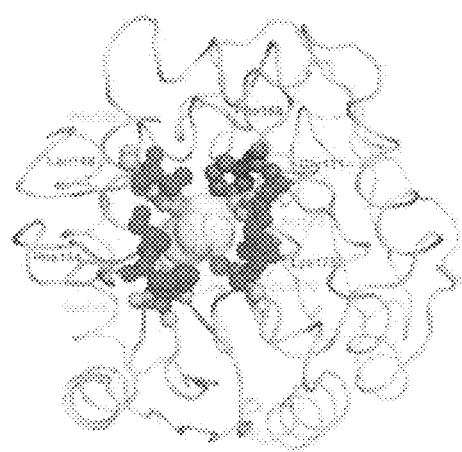
FIG. 2. Residues lining the access tunnel of haloalkane dehalogenase DhaA from *Rhodococcus rhodochrous* NCIMB 13064. Residues Phe144, Ala145, Thr148, Phe149, Gly171, Ala172, Lys175, Cys176 and Val245 were identified in the proximity of the access tunnel of DhaA (PDB: 1CQW) by Hotspot Wizard v1.6 (Pavelka, A., Chovancova, E., and Damborsky, J. 2009: HotSpot Wizard: a web server for identification of hot spots in protein engineering. Nucleic Acids Research 37: 376-383) and marked by color according to their expected mutability: red—high, yellow—average and blue—low mutability. The surface of the access tunnel is shown in transparent gray. The figure was created using PyMOL v1.2.8 (DeLano Scientific, San Francisco, Calif., USA).

Engineering a Thermostable and Solvent Resistant Haloalkane Dehalogenase DhaA by Modification of Bottleneck in its Access Tunnel using a Combination of Rational Design and Directed Evolution Introduction Substitutions localized at the protein surface are believed to be structurally more acceptable than mutations in the enzyme interior and mostly without a detrimental effect on its activity (Eijsink, V. G. H., Gåseidnes, S., Borchert, T. V., a van den Burg, B. 2005: Directed evolution of enzyme stability. Biomolecular Engineering 22: 21-30). Less-frequently occurring tunnel residues represent a good target for mutagenesis. Substitutions in these natural hotspots (FIG. 2) do not disrupt the active site architecture accompanied by loss of functionality (Pavlova, M., Klvana, M., Prokop, Z., Chaloupkova, R., Banas, P., Otyepka, M., Wade, R. C., Tsuda, M., Nagata, Y., a Damborsky, J. 2009: Redesigning dehalogenase access tunnels as a strategy for degrading an anthropogenic substrate. Nature Chemical Biology 5: 727-733). Here we demonstrate that substitutions of only four tunnel residues forming the bottleneck of the haloalkane dehalogenase DhaA from *Rhodococcus rhodochrous* NCIMB 13064 are sufficient for significant improvement of enzyme structural and kinetic stability under elevated temperature and in the presence of organic solvent.

Methods

Gene Manipulations.

Oligonucleotides were designed according to the nucleotide sequence of DhaA or its mutant variants, and artificially synthesized in the Core Laboratory of the Masaryk University (Brno, Czech Republic). The used recombinant gene dhaA-His$_6$, carrying restriction sites for BamHI and HindIII and C-terminal hexahistidine tag, was previously subcloned into pAQN (Pavlova, M., Klvana, M., Prokop, Z., Chaloupkova, R., Banas, P., Otyepka, M., Wade, R. C., Tsuda, M., Nagata, Y., a Damborsky, J. 2009: Redesigning dehalogenase access tunnels as a strategy for degrading an anthropogenic substrate. Nature Chemical Biology 5: 727-733). The ampicillin-resistant vector pAQN carrying the multiple cloning site from pUC18 was utilized in present study for both basic cloning manipulations and for overexpression of enzyme variants. DhaA variants were expressed under the control of tac promoter. Their expression was repressed by the product of lacI$^q$ gene carried by pAQN and started after the addition of the inductor isopropyl-β-D-thiogalactoside (IPTG). The compatible *Escherichia coli* strains used were DH5α, BL21 and XJb (Zymo Research, Orange, USA). Plasmid DNA of selected variants was isolated by GeneJet Plasmid Miniprep Kit (Fermentas, Burlington, Canada). QIAquick PCR purification or Gel Extraction kits (Qiagen, Hilden, Germany) were used for purification of DNA fragments. Established methods were applied for following procedures: digestion of plasmid DNA and PCR-amplified DNA fragments with restriction endonucleases, agarose gel electrophoresis, sticky-end and blunt-end DNA ligation, and transformation to *E. coli* cells.

Error-Prone PCR (epPCR).

Random mutagenesis of dhaAHis$_6$ was set in five microtubes of which content was subsequently mixed. Parameters according to Schmidt et al. were selected as starting conditions (Schmidt, M., Hasenpusch, D., Kähler, M., Kirchner, U., Wiggenhorn, K., Langel, W., a Bornscheuer, U. T. 2006: Directed evolution of an esterase from *Pseudomonas fluorescens* yields a mutant with excellent enantioselectivity and activity for the kinetic resolution of a chiral building block. ChemBioChem 7: 805-809). The 20 µl reaction mixture contained 0.1 ng of template DNA, 10 pmol of each oligonucleotide, imbalanced mixture of dNTPs (0.2 mM dATP, 0.2 mM dGTP, 1 mM dTTP and 1 mM dCTP), mutation buffer (7 mM MgCl$_2$, 50 mM KCl, 10 mM Tris pH 8, 0.01% (w/v) gelatine), 0.05 mM MnCl$_2$ and 1 U of GoTaq polymerase (Promega, Madison, USA). EpPCR proceeded under following conditions: 2 min at 95° C. and then 24 cycles of 30 s at 95° C., 30 s at 58° C., 60 s at 72° C.; followed by 7 min at 72° C. Yield and purity of epPCR reactions were checked in 2% agarose gel. The parental DNA was eliminated by methylation-dependent endonuclease DpnI and epPCR products were subcloned into the Antarctic phosphatase treated pAQN vector using BamHI and HindIII restriction sites. Successfulness of ligation was checked by colony PCR. The 5 µl reaction mixture consisted of a part of the bacterial colony, 0.125 pmol of each oligonucleotide, 0.2 mM dNTPs, reaction buffer B and 0.2 U of yellow Taq DNA polymerase (Eurx, Gdansk, Germany). PCR ran under these conditions: 5 min at 95° C., and then 5 cycles of 30 s at 95° C., 30 s at 63° C. and 60 s at 72° C.; followed by 25 cycles of 30 s at 95° C., 30 s at 58° C. and 60 s at 72° C.; finished by 7 min at 72° C. Presence of products was checked in 2% agarose gel.

Saturation Mutagenesis.

Saturation mutagenesis at variable position 171 was carried out by inverse PCR using a synthetic oligonucleotide with one degenerated NNK codon and Phusion High-Fidelity PCR kit (Finnzymes, Espoo, Finland). N means an equal mixture of all four deoxyribonucleotides and K an equal mixture of deoxyguanylate and deoxythymidylate. The entire plasmid pAQN-dhaA80His$_6$, which was used as a template, was amplified according to the manufacturer's recommendations. The 50 µL reaction mixture contained 10 ng of template DNA, 5 pmol of each oligonucleotide, 0.2 mM dNTPs, Phusion HF buffer with 1.5 mM $MgCl_2$ and 1 U of Phusion DNA Polymerase. PCR proceeded under following conditions: 30 s at 98° C., and then 34 cycles of 10 s at 98° C., 30 s at 65° C. and 150 s at 72° C.; followed by 10 min at 72° C. Yield and purity of PCR products were checked in the 0.8% agarose gel. PCR products were treated by DpnI and their ends were subsequently connected by blunt ligation using T4 DNA polynucleotide kinase and T4 DNA ligase.

Site-Directed Mutagenesis.

Mutant recombinant genes dhaA60His$_6$, dhaA61His$_6$ and dhaA80His$_6$ were obtained using QuikChange Site-Directed Mutagenesis Kit (Stratagene, La Jolla, USA) according to manufacturer's instructions. Specific complementary oligonucleotides were designed for introducing of mutations. His$_6$dhaA63 and His$_6$dhaA82 genes were synthesized artificially (Entelechon and Mr. Gene, Regensburg, Germany) and subcloned into the expression vector pAQN using BamHI and HindIII restriction sites.

Construction of Mutant Libraries.

Mutant libraries were propagated in *E. coli* XJb, an autolysis strain derived from *E. coli* BL21 with chromosomal insertion of λ lysozyme gene inducible by arabinose. Constructed plasmids were transformed into *E. coli* XJb cells using the standard electroporation protocol. Transformation mixture was put in the electroporation cuvette with 0.1 cm gap (Bio-Rad, Hercules, USA or BTX, Holliston, USA). The pulse 1.8 kV was delivered by Bio-Rad MicroPulser (Hercules, USA) or ECM 399 Generator (BTX, Holliston, USA). Ten candidates from each library were randomly selected for sequence analysis.

Cultivation in Microplates.

The sterile microplate wells were filled with 150 μl of Luria-Bertani (LB) medium with ampicillin (of a final concentration 100 μg ml$^{-1}$). Wells were inoculated by single colonies using sterile tooth-picks. *E. coli* XJb pAQN-dhaA-His$_6$ cells were used for inoculation of four positive controls for basal activity whereas *E. coli* XJb cells carrying an empty vector pAQN were applied as four negative controls in the screening of epPCR library. *E. coli* XJb pAQN-dhaA80His cells were used as a positive control for the basal activity in the screening after saturation mutagenesis. Cultures were grown overnight at 37° C. at 200 r.p.m. After 14 hrs of cultivation ($OD_{600}$=0.4 in a microplate), 50 μl of each culture from the cultivation plate was added to 50 μl of 30% glycerol and thus the replica plate used for storage was created. Then, 100 μl of fresh LB medium with ampicillin, L-arabinose (of a final concentration 3 mM) and IPTG (of a final concentration 0.5 mM) were added to each well of the cultivation plate. Microplates were cultivated at 30° C. at 180 r.p.m. for 4 hrs. Cell cultures were harvested and frozen at −80° C.

Screening Assay.

The method described by Holloway et al. (Holloway, P., Trevors, J., and Lee, H. 1998: A colorimetric assay for detecting haloalkane dehalogenase activity. Journal of Microbiological Methods 32: 31-36) was carried out with modifications. The pH indicator phenol red is sensitive to pH changes and turns yellow if pH decreases below 6.8. After 10 min at room temperature, 50 μl of the lysis buffer (1 mM HEPES, 20 mM $Na_2SO_4$ and 1 mM EDTA, pH 8.2) were added to each well of defrosted plates. Cell debris was removed from lysate by centrifugation at 1,600 g for 30 min after one-hour-long incubation at 650 r.p.m. at room temperature. Then 20 μl of lysate were transferred into each well of a new microplate and 180 μl of assay buffer (DMSO, 1 mM HEPES, 20 mM $Na_2SO_4$ and 1 mM EDTA, pH 8.2) with 1,2-dibromoethane (12.1 mM) were added. EpPCR and saturation mutagenesis libraries were screened in the presence of 42% and 52% (v/v) DMSO, respectively. Substrate was incubated in the reaction buffer for 30 min at 37° C. before starting the reaction. The microplate was closed by the lid and parafilm for 14 h. Then the reaction mixture was diluted by buffer containing pH indicator phenol red (1 mM HEPES, 20 mM $Na_2SO_4$ and 1 mM EDTA, 50 μg ml$^{-1}$ phenol red, pH 8.2). The change in color of pH indicator was estimated at 540 nm by spectrophotometer as was previously described by Holloway (Holloway, P., Trevors, J., and Lee, H. 1998: A colorimetric assay for detecting haloalkane dehalogenase activity. Journal of Microbiological Methods 32: 31-36).

Expression and Purification of Proteins.

Recombinant plasmids with the mutant variants were transformed into *Escherichia coli* BL21. For overexpression, cells were grown at 37° C. to an optical density ($OD_{600}$) about 0.6 in 1 l of LB medium with ampicillin (100 μg ml$^{-1}$). Cultures were incubated for approximately 3 hrs at the rate of 150 r.p.m. Protein expression was induced by adding IPTG to a final concentration 0.5 mM in LB medium and the temperature was decreased to 30° C. Cells were harvested by 12 min centrifugation at 3,700 g after 4 hrs of cultivation. During harvesting, cells were washed once with 50 mM phosphate buffer (pH 7.5) and then resuspended in 20 ml of phosphate buffer. Harvested cells were kept at −80° C. overnight. Defrosted cultures were disrupted by sonication with the ultrasonic processor Hielscher UP200S (Hielscher Ultrasonics, Teltow, Germany). Lysates were centrifuged at 21,000 g for 1 h. The crude extracts were applied on Ni-NTA Superflow Cartridge (Qiagen, Hilden, Germany) charged with $Ni^{2+}$ and equilibrated with purification buffer of pH 7.5 composed of 16.4 mM $K_2HPO_4$, 3.6 mM $KH_2PO_4$ and 0.5 M NaCl containing 10 mM imidazole. Unbound and weakly bound fractions were washed out with purification buffer containing 50 mM imidazole. Histidine-tagged proteins were eluted with purification buffer containing 300 mM imidazole. The eluted proteins were dialyzed against 50 mM phosphate buffer (pH 7.5). Protein concentrations were determined by the Bradford reagent (Sigma-Aldrich, St. Louis, USA) with bovine serum albumin as a standard. Purity of purified proteins was checked by SDS-polyacrylamide gel electrophoresis in 15% polyacrylamide gels. The gels were stained by Coomassie brilliant blue R-250 dye (Fluka, Buchs, Switzerland) and molecular mass of proteins was determined based on Protein Molecular Weight Marker (Fermentas, Burlington, Canada).

Circular Dichroism (CD) Spectroscopy.

CD spectra were recorded at room temperature (23° C.) using Jasco J-810 spectropolarimeter (Jasco, Tokyo, Japan) equipped with the Peltier cell holder. Data were collected from 185 to 260 nm, at 100 nm min$^{-1}$, 1 s response time and 2 nm bandwidth with a 0.1 cm quartz cuvette. The concentration of examined enzymes was in the range of 0.15-0.25 mg ml$^{-1}$. The spectra represent the average of ten individual scans and were corrected for absorbance caused by the buffer. Collected CD data are expressed in terms of the mean residue ellipticity (Θ MRE). Thermal unfolding of tested enzymes was followed by monitoring the ellipticity at 222 nm over the temperature range from 20 to 80° C., with a resolution 1° C., at a heating rate 1° C. min$^{-1}$. Recorded thermal denaturation curves were fitted to sigmoidal curves using the software Origin 6.1 (OriginLab, Massachusetts, USA) and melting temperature ($T_m$), which is the temperature at which half of the enzyme is in unfolded state (Polizzi, K. M., Bommarius, A. S., Broering, J. M., a Chaparro-Riggers, J. F. 2007: Stability of biocatalysts. Current Opinion in Chemical Biology 11: 220-225), was evaluated as a midpoint of the normalized thermal transition.

Fluorescence Spectroscopy.

The enzymes stored in 50 mM phosphate buffer (pH 7.5) were diluted with DMSO to the final concentration 0, 10, 20, 30, 40, 50, 55, 60, 65, 70 and 80% (v/v). Fluorescence spectra were scanned with spectrofluorimeter FluoroMax-4P (HORIBA Jobin Yvon, New Jersey, USA) from 270 to 450 nm: i) immediately at 23° C. and ii) after incubation of the sample at 37° C. for 30 min. Fluorescence emission spectra were measured with scan speed 50 nm per minute using 0.5 cm quartz cuvette. The excitation and emission bandwidth was 1 nm and used excitation wavelength was 280 nm. Each spectrum was corrected for fluorescence intensity caused by the mixture of buffer and DMSO and related to enzyme concentration (approx. 0.25 mg ml$^{-1}$). The shifts in emission maximum of samples with different concentration of DMSO were observed. Half-concentration $C_{1/2}$, which is the (v/v) concentration of DMSO needed to unfold half of the enzyme (Polizzi, K. M., Bommarius, A. S., Broering, J. M., a Chaparro-Riggers, J. F. 2007: Stability of biocatalysts. Current Opinion in Chemical Biology 11: 220-225), was estimated as the inflection point of the sigmoidal dependence of the wavelength of emission maximum on the concentration of denaturant.

Steady-State Kinetics and Kinetic Half-Life Assays.

Dehalogenase activities of individual enzyme variants in the absence and presence of 40% (v/v) DMSO were measured using reagents containing mercuric thiocyanate and ferric ammonium sulfate (Iwasaki, I., Utsumi, S., a Ozawa, T. 1952: New colorimetric determination of chloride using mercuric thiocyanate and ferric ion. Bulletin of the Chemical Society of Japan 25: 226-226). The halide ions released during the reaction were quantified by an end-point spectrophotometric measurement. Reactions were carried out in 25 ml Microflasks closed by Mininert valves (Alltech, Deerfield, USA) at 37° C. Reaction mixture contained 1,2-dibromoethane dissolved in 100 mM glycine buffer (pH 8.6) or 60 mM glycine buffer (pH 8.6) with 40% (v/v) DMSO. The initial activity measurements were carried out at least at twelve different substrate concentrations (0.2-32 mM). The initial concentrations of 1,2-dibromoethane in the reaction mixture were established on gas chromatograph GC Trace 2000 (Thermo Fisher Scientific, Waltham, USA) equipped with flame ionization detector and capillary column DB-FFAP 30 m×0.25 mm×0.25 μm (J&W Scientific, Folsom, USA). Samples were periodically withdrawn with a 1 ml syringe (Hamilton, Reno, USA) during 30 min measurement after the initiation of the reaction by the addition of an enzyme. As deactivation of DhaA proceeded rapidly in 40% (v/v) DMSO, samples were withdrawn during 3 min in this case. All withdrawn samples were immediately mixed with 35% nitric acid to stop the reaction. The reagents with mercuric thiocyanate and ferric ammonium sulfate were subsequently added to the collected samples and absorbance of the final mixture was measured at 460 nm. The specific activities were quantified by an initial linear slope of the increasing halide concentration in time after the subtraction of spontaneous hydrolysis of 1,2-dibromoethane. The kinetic constants were calculated using a non-linear fitting in the program Origin version 6.1 (OriginLab, Massachusetts, USA). The same technique was used for the measurement of enzyme half-lives ($\tau_{1/2}$) at the fixed concentration of 1,2-dibromoethane (12.1 mM) in the presence of DMSO. The reaction mixture containing 60 mM glycine buffer (pH 8.6), 40% (v/v) DMSO and enzyme were incubated in time (0-4000 h) at 37° C. After the initiation of the reaction by the addition of substrate, samples were periodically withdrawn during 30 min measurement. As deactivation of DhaA, DhaA60 and DhaA82 proceeded rapidly these samples were withdrawn during only 120-second-long measurement. Half-lives ($\tau_{1/2}$) were calculated as $\tau_{1/2}=\ln 2/-k$, where k, representing the deactivation rate constant, which corresponds to the negative slope from the dependence of natural logarithm of relative activity on time in mM (Polizzi, K. M., Bommarius, A. S., Broering, J. M., a Chaparro-Riggers, J. F. 2007: Stability of biocatalysts. Current Opinion in Chemical Biology 11: 220-225).

Results

Figure 3:
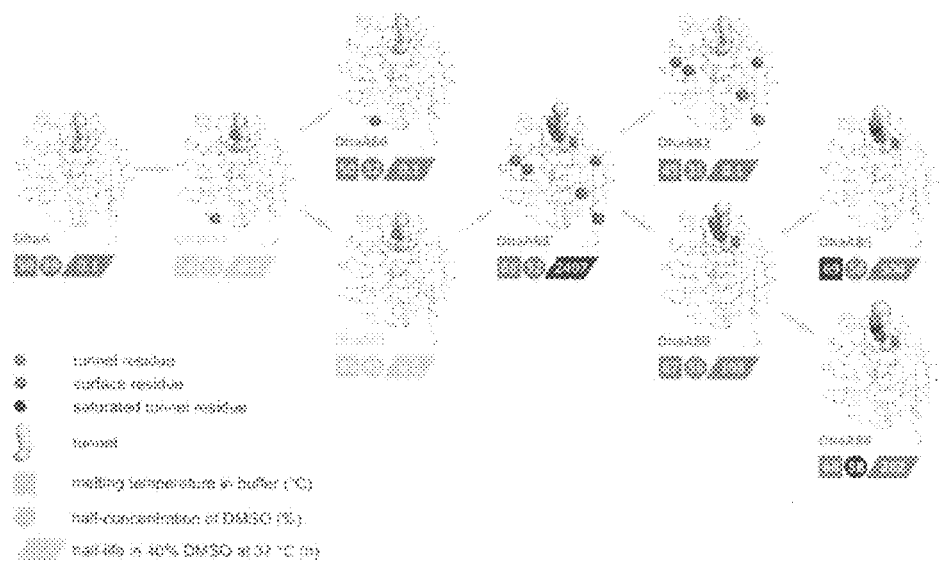
FIG. 3. Improvement of haloalkane dehalogenase DhaA stability by engineering the bottleneck of its access tunnel. Structural thermostability was measured as the melting temperature ($T_m$) in 50 mM buffer (pH 7.5). Structural resistance to DMSO was determined as the half-concentration ($C_{1/2}$) of DMSO in the mixtures of 50 mM phosphate buffer (pH 7.5) and DMSO after 30-minute-long incubation at 37° C. Kinetic stability (half-lives in hours, $t_{1/2}$) was calculated from residual activities towards 12.1 mM 1,2-dibromoethane in the mixture of 60 mM glycine buffer (pH 8.6) and 40% (v/v) DMSO at 37° C. in time. The color of shapes indicates improvement of stability compared to the wild-type enzyme: blue—no improvement, yellow—improvement, red—substantial improvement, and black—the best value. $^a$Mutant prepared by the gene site saturation mutagenesis (Gray, K., Richardson, T., Kretz, K., Short, J., Bartnek, F., Knowles, R., Kan, L., Swanson, P., a Robertson, D. 2001: Rapid evolution of reversible denaturation and elevated melting temperature in a microbial haloalkane dehalogenase. Advanced Synthesis and Catalysis 343: 607-617).

Eight different protein variants were obtained by the site-directed mutagenesis (DhaA60, DhaA61, DhaA80 and DhaA82), random directed evolution (DhaA57 and DhaA63) and saturation mutagenesis (DhaA85 and DhaA88); each variant was structurally and biochemically characterized (Table 1). Mutations introduced into the bottleneck of the access tunnel were essential for the improved structural and kinetic stability of the variants, while the variants carrying surface mutations exhibit similar stability parameters as the wild-type enzyme (FIG. 3).

TABLE 1

Substitutions introduced to the individual DhaA variants.

| Variant | Position | | | | | | | | | | |
|---|---|---|---|---|---|---|---|---|---|---|---|
| | 78 | 80 | 95 | 148[a] | 171[a] | 172[a] | 176[a] | 227 | 240 | 291 | 292 |
| DhaA[b] | D | F | L | T | G | A | C | N | W | P | A |
| DhaA57[b] | D | F | V | T | G | V | C | N | W | P | A |
| DhaA60[b] | D | F | V | T | G | A | C | N | W | P | A |
| DhaA61[b] | D | F | L | T | G | V | C | N | W | P | A |
| DhaA63[c] | G | S | L | L | Q | V | F | T | Y | G | G |
| DhaA80[b] | D | F | L | L | Q | V | F | N | W | P | A |
| DhaA82[c] | G | S | L | T | G | A | C | T | Y | G | G |
| DhaA85[b] | D | F | L | L | V | V | F | N | W | P | A |
| DhaA88[b] | D | F | L | L | L | V | F | N | W | P | A |

[a] in the access tunnel;
[b] C-terminal hexahistidine tag: HHHHHH;
[c] N-terminal hexahistidine tag: MGDSHHHHHHG.
Substituted residues are marked by gray color.
For clarity, residues in DhaA63 and DhaA82 are numbered without counting residues of the N-terminal hexahistidine tag.

Figure 4:
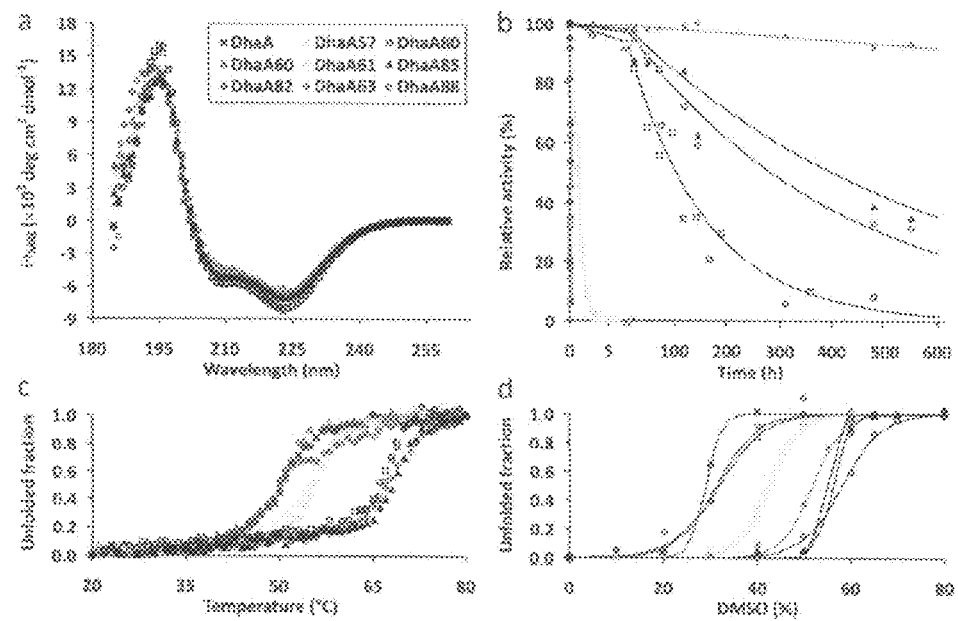
FIG. 4. Structural and kinetic characteristics of haloalkane dehalogenase DhaA variants. (a) Far-UV circular dichroism spectra of folded enzymes in 50 mM phosphate buffer (pH 7.5). (b) Thermal denaturation in 50 mM phosphate buffer (pH 7.5). Only every 10th point is shown. (c) Structural resistance to DMSO was tested in the mixtures of 50 mM phosphate buffer (pH 7.5) and DMSO after 30-minute-long incubation at 37° C. (d) Kinetic stability was measured as the residual activity towards 12.1 mM 1,2-dibromoethane in the mixture of 60 mM glycine buffer (pH 8.6) and 40% (v/v) DMSO at 37° C. in time.

Four mutations introduced cumulatively to bottleneck of the access tunnel of haloalkane dehalogenase DhaA resulted in properly folded variants with improved kinetic stability in 40% (v/v) DMSO 4000-fold and elevated structural thermostability by 19° C. (FIGS. 3 and 4).

Conclusions

Here we demonstrate that iterative saturation mutagenesis of the residues forming the bottleneck of the access tunnel is a generally-applicable method for improving stability of enzymes with buried active sites at elevated temperatures and in the presence of organic solvents. The target tunnel residues can be easily predicted by freely available bioinformatics software, e.g., Hotspot Wizard (Pavelka, A., Chovancova, E., a Damborsky, J. 2009: HotSpot Wizard: a web server for identification of hot spots in protein engineering. Nucleic Acids Research 37: W376-383). Systematic mutagenesis of the residues located in the bottleneck of the access tunnel followed by screening or selection is an efficient way of constructing robust biocatalysts.

Example 2

Engineering a Thermostable Haloalkane Dehalogenase LinB by Modification of Bottleneck Residue of its Access Tunnel using Rational Design Introduction The surface residue of the haloalkane dehalogenase LinB in the position 177 was selected for modification based on structural and phylogenetic analysis. This residue makes the bottleneck of the access tunnel and it is the most variable residue of the active site pocket among different haloalkane dehalogenases. Nineteen amino acid residues were introduced to the position 177 by random mutagenesis to investigate its effect on catalytic properties (Chaloupkova, R., Sykorova, J., Prokop, Z., Jesenska, A., Monincova, M., Pavlova, M., Tsuda, M., Nagata, Y., and Damborsky, J. 2003: Modification of activity and specificity of haloalkane dehalogenase from *Sphingomonas paucimobilis* UT26 by engineering of its entrance tunnel. Journal of Biological Chemistry 278: 52622-52628). Two protein variants (L177E and L177N) from nineteen prepared proteins could not be overexpressed in *E. coli* and other two variants (L177P and L177I) did not show activity with any of tested substrates. Successfully purified and active enzymes were kinetically characterised by determination of their specific activities with 12 different substrates and the collected data were quantitatively analysed using the multivariate statistics. This statistical analysis revealed that catalytic activity of mutant enzymes generally increased with the introduction of small and non-polar amino acid in the position 177. Here we show that all active mutant variants of LinB are correctly folded and display very different thermal stabilities.

Methods

Circular Dichroism Spectroscopy.

Circular dichroism spectra were recorded at 20° C. using a Jasco J-810 spectrometer (Jasco, Tokyo, Japan) coupled with Peltier temperature controller. Data were collected from 185 to 260 nm, at 100 nm/min, 1 s response time and 2 nm bandwidth using a 0.1 cm quartz cuvette containing the enzyme variant in 50 mM potassium phosphate buffer (pH 7.5). Each spectrum shown is the average of ten individual scans and was corrected for absorbance caused by the buffer. CD data were expressed in terms of the mean residue ellipticity ($\Theta_{MRE}$) using the equation:

$$\Theta_{MRE} = \frac{(\Theta_{obs} \cdot M_w \cdot 100)}{n \cdot c \cdot l}$$

were $\Theta_{obs}$ is the observed ellipticity in degrees, $M_w$ is the protein molecular weight, n is number of residues, l is the cell path length (0.1 cm), c is the protein concentration and the factor 100 originates from the conversion of the molecular weight to mg/dmol.

Thermal Denaturation.

Thermal unfolding of LinB enzyme variants was followed by monitoring the ellipticity at 222 nm over the temperature range of 20 to 80° C., with a resolution 0.1° C., at a heating rate 1° C./min. Recorded thermal denaturation curves were roughly normalized to represent signal changes between approximately 1 and 0 and fitted to sigmoidal curves using software Origin 6.1 (OriginLab, Massachusetts, USA). The melting temperatures ($T_m$) were evaluated as a midpoint of the normalized thermal transition.

Results

Figure 5:
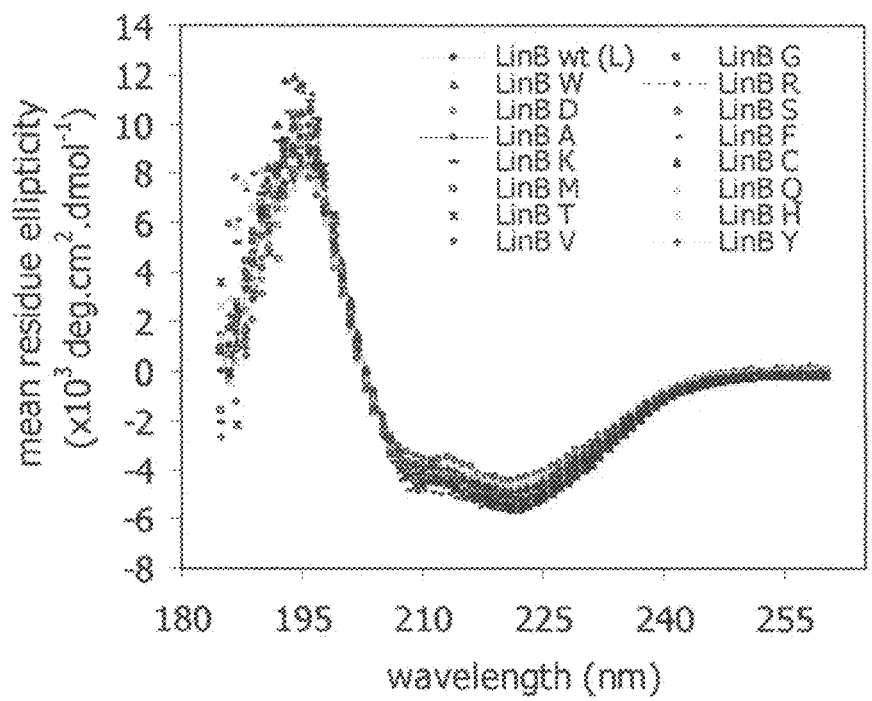
FIG. 5. Far-UV circular dichroism spectra of wild type haloalkane dehalogenase LinB and its variants in the position 177.

Far-UV CD spectra were used to assess the proper folding and secondary structure of fifteen mutant variants of haloalkane dehalogenase LinB. Almost no difference between the spectrum of LinB wt and its mutant variants was observed (FIG. 5). All enzymes showed CD spectra typical of predominantly α-helical conformation with two negative features at 222 and 208 nm; and a positive peak at 195 nm (Fasman, G. D. 1996: Circular Dichroism and the Conformational Analysis of Biomolecules, Plenum Press, New York, p. 740). This indicates that inserted mutations have almost no effect on secondary structure of all tested LinB variants.

Thermally induced denaturation was tested to detect the effect of amino acid substitution in the position 177 on thermal stability of prepared LinB variants. Four out of fifteen constructed variants (L177G, L177W, L177K and L177Y) exhibited improvement in thermal stability (Table 2). Five variants (L177D, L177A, L177C and L177T) showed decrease in melting temperature. The rest of the variants exhibited no change in thermal stability, compared to the wild type enzyme. The best thermostability was detected for L177W, whose melting temperature lies about 5° C. higher than the melting temperature of wild type.

TABLE 2

Melting temperatures of LinB variants with rationally modified bottleneck of the access tunnel.

| Enzyme variant | $T_m$ (° C.) | $\Delta T_m$ (° C.) |
|---|---|---|
| Wild type | 48.03 ± 0.52 | — |
| L177G | 51.17 ± 0.37 | 3.1 |
| L177W | 53.13 ± 0.02 | 5.1 |
| L177R | 47.37 ± 0.17 | −0.7 |
| L177D | 42.51 ± 0.39 | −5.5 |
| L177S | 47.00 ± 0.15 | −1.0 |
| L177A | 46.88 ± 0.27 | −1.2 |
| L177F | 47.28 ± 0.52 | −0.8 |
| L177K | 51.01 ± 0.54 | 3.0 |
| L177C | 45.00 ± 0.40 | −3.0 |
| L177M | 47.78 ± 0.17 | −0.3 |
| L177Q | 48.08 ± 0.17 | 0.0 |
| L177T | 43.19 ± 0.26 | −4.8 |
| L177H | 48.85 ± 0.28 | 0.8 |
| L177V | 48.65 ± 0.42 | 0.6 |
| L177Y | 49.06 ± 0.45 | 1.0 |

Conclusions

Comparison of measured CD spectra demonstrates that all prepared mutant variants of LinB are correctly folded. Introduced mutations into the position 177 did not alter secondary structure of LinB enzyme, yet they significantly affected its thermal stability. The thermostability was improved in the LinB mutants L177Y, L177K, L177G and L177W, which showed improvement in the melting temperatures 1.0, 3.0, 3.1 and 5.1° C., respectively.

Example 3

Design of Thermostable Proteins by Targeted Modifications of the Access Tunnels Introduction In this example, in silico design of protein variants with modified access tunnels and estimated effect of the mutations on protein stability is presented. Six enzymes (Table 3), possessing very different protein fold and enzymatic activity, were used in this study: methane monooxygenase (Elango, N., Radhakrishnan, R., Froland, W. A., Wallar, B. J., Earhart, C. A., Lipscomb, J. D., and Ohlendorf, D. H. 1997: Crystal structure of the hydroxylase component of methane monooxygenase from *Methylosinus trichosporium* OB3b, Protein Science 6: 556-568), type II cholesterol oxidase (Coulombe, R., Yue, K. Q., Ghisla, S., and Vrielink, A. 2001: Oxygen access to the active site of cholesterol oxidase through a narrow channel is gated by an Arg-Glu pair, Journal of Biological Chemistry 276: 30435-30441), Ni—Fe hydrogenase (Volbeda, A., Martin, L., Cavazza, C., Matho, M., Faber, B. W., Roseboom, W., Albracht, S. P. J., Garcin, E., Rousset, M., and Fontecilla-Camps, J. C. 2005: Structural differences between the ready and unready oxidized states of (NiFe) hydrogenases, Journal of Biological Inorganic Chemistry 10: 239-249), curcuminoid synthase (Morita, H., Wanibuchi, K., Nii, H., Kato, R., Sugio, S., and Abe, I. 2010: Structural basis for the one-pot formation of the diarylheptanoid scaffold by curcuminoid synthase from *Oryza sativa*, Proceedings of the National Academy of Sciences of USA 107: 19778-19783), acetylcholinesterase (Dvir, H., Jiang, H. L., Wong, D. M., Harel, M., Chetrit, M., He, X. C., Jin, G. Y., Yu, G. L., Tang, X. C., Silman, I., Bai, D. L., and Sussman, J. L. 2002: X-ray structures of *Torpedo californica* acetylcholinesterase complexed with (+)-huperzine A and (−)-huperzine B: structural evidence for an active site rearrangement, Biochemistry 41: 10810-10818) and epoxide hydrolase (Zou, J., Hallberg, B. M., Bergfors, T., Oesch, F., Arand, M., Mowbray, S. L., and Jones, T. A. 2000: Structure of *Aspergillus niger* epoxide hydrolase at 1.8 A resolution: implications for the structure and function of the mammalian microsomal class of epoxide hydrolases, Structure 8: 111-122). The results clearly show wide applicability of the tunnel engineering approach for the design of enzymes with improved thermal stability.

Methods

Identification of Residues Lining the Access Tunnels.

Tunnels and their forming residues were identified by CAVER software (Petrek, M., Otyepka, M., Banas, P., Kosinova, P., Koca, J., and Damborsky, J. 2006: CAVER: a new tool to explore routes from protein clefts, pockets and cavities, BMC Bioinformatics 7: 316). Protein ID, coordinates of starting point, number of amino acids of whole protein or selected tunnel and number of stabilizing mutations and positions within the tunnel are summarized in Table 3.

Prediction of Stabilization Effects.

Individual crystal structures were first repaired by <RepairPDB> module of FoldX v. 3.0 beta5. (Guerois, R., Nielsen, J. E., and Serrano, L. 2002: Predicting changes in the stability of proteins and protein complexes: a study of more than 1000 mutations, Journal of Molecular Biology 320: 369-387). For each tunnel residue, stabilization effects of all possible single-point mutations were estimated using the FoldX <BuildModel> module. Calculations were performed 5-times for each mutant using following protocol: pH 7, temperature 298 K, ion strength 0.050 M, VdWDesign 2. The mutations showing the change in the Gibbs free energy $\Delta\Delta G < -0.5$ kcal/mol were regarded as stabilizing. Predictions with high standard deviations or significant improvement of the Van der Waal's clash energy should be interpreted with caution.

Results

Methane Monooxygenase Hydroxylase.

Figure 6:
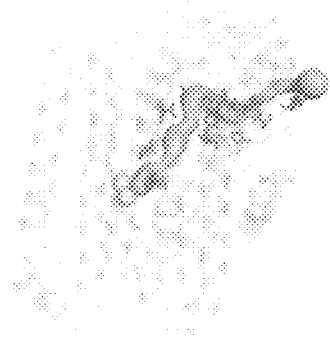
FIG. 6. Structure of methane monooxygenase hydroxylase. Overall enzyme structure is represented in gray cartoon, amino acid positions that stabilize enzyme are in red stick, tunnel is in gold surface.

Methane monooxygenase hydroxylase (MMOH) from aerobic methanotrophic bacterium *Methylosinus trichosporium* OB3b, catalyzes the $O_2$-dependent conversion of methane to methanol. The two irons of the active site cluster of MMOH are connected with protein surface via approximately 58 Å long tunnel. List of selected mutations with predicted $\Delta\Delta G$ and standard deviation of different run results are presented in Table 4. Selected residues and the tunnel are visualized in FIG. 6.

TABLE 4

Predicted $\Delta\Delta G$ and standard deviation of different run results of selected tunnel mutants of methane monooxygenase hydroxylase.

| Residue | Position | Mutation | $\Delta\Delta G$ [kcal/mol] | SD |
|---|---|---|---|---|
| V | 105 | L | −1.23 | 0.15 |
| V | 105 | Y | −1.18 | 0.34 |
| V | 105 | F | −0.76 | 0.06 |

TABLE 3

Analyzed proteins and parameters of tunnel calculation.

| Enzyme | PDB-ID | Chain | Coordinates of starting point | | | Number of amino acids | | number of stabilizing mutations in the tunnel[a] | number of stabilizing positions in the tunnel[a] |
|---|---|---|---|---|---|---|---|---|---|
| | | | X | Y | z | entire protein | selected tunnel | | |
| Methane monooxygenase | 1MHY | D | −39.21 | 77.31 | 24.55 | 521 | 34 | 39 | 11 |
| Type II cholesterol oxidase | 1I19 | A | 15.92 | 44.43 | 57.13 | 561 | 15 | 16 | 8 |
| Ni—Fe Hydrogenase | 1YQW | A | 7.11 | −0.31 | 16.16 | 264 | 26 | 40 | 12 |
| Curcuminoid synthase | 3ALE | D | 19.13 | 45.43 | 53.61 | 416 | 12 | 16 | 3 |
| Acetylcholinesterase | 1EA5 | A | 4.60 | 66.27 | 61.95 | 537 | 22 | 17 | 5 |
| Epoxide hydrolase | 1QO7 | B | 33.12 | 30.34 | 83.67 | 394 | 12 | 14 | 5 |

[a]The residues located at the protein exterior and forming the active site were excluded from the analysis.

TABLE 4-continued

Predicted ΔΔG and standard deviation of different run results of selected tunnel mutants of methane monooxygenase hydroxylase.

| Residue | Position | Mutation | ΔΔG [kcal/mol] | SD |
|---|---|---|---|---|
| V | 105 | M | −0.70 | 0.08 |
| L | 110 | M | −0.66 | 0.06 |
| P | 179 | F | −1.25 | 0.05 |
| P | 179 | M | −0.70 | 0.10 |
| T | 213 | M | −2.65 | 0.01 |
| T | 213 | R | −2.32 | 0.29 |
| T | 213 | L | −2.24 | 0.03 |
| T | 213 | K | −1.50 | 0.28 |
| T | 213 | H | −1.15 | 0.35 |
| T | 213 | Q | −1.08 | 0.19 |
| T | 213 | I | −1.01 | 0.01 |
| T | 213 | A | −0.97 | 0.02 |
| A | 349 | I | −2.77 | 0.20 |
| A | 349 | M | −2.42 | 0.33 |
| A | 349 | F | −2.01 | 0.29 |
| A | 349 | V | −1.47 | 0.01 |
| A | 349 | L | −0.79 | 0.13 |
| A | 350 | M | −2.64 | 0.03 |
| A | 350 | L | −1.97 | 0.16 |
| A | 350 | Q | −0.73 | 0.04 |
| G | 357 | F | −1.96 | 0.22 |
| G | 357 | M | −1.38 | 0.02 |
| G | 357 | D | −1.22 | 0.02 |
| G | 357 | Y | −1.16 | 0.02 |
| G | 357 | L | −1.10 | 0.08 |
| H | 382 | W | −0.98 | 0.14 |
| H | 382 | M | −0.74 | 0.18 |
| H | 413 | F | −2.34 | 0.01 |
| H | 413 | Y | −1.80 | 0.04 |
| H | 413 | M | −1.47 | 0.13 |
| H | 413 | L | −1.06 | 0.10 |
| H | 413 | K | −0.69 | 0.07 |
| V | 415 | I | −1.12 | 0.01 |
| V | 415 | L | −0.84 | 0.06 |
| P | 424 | M | −0.91 | 0.04 |
| P | 424 | L | −0.84 | 0.04 |

Cholesterol Oxidase.

Figure 7:
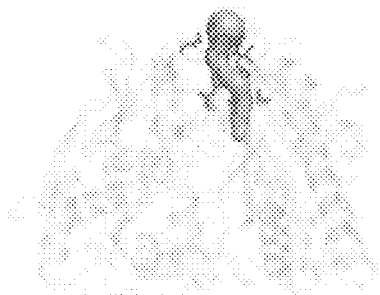
FIG. 7. Structure of type II cholesterol oxidase BsChOx from *Brevibacterium sterolicum*. Overall enzyme structure is represented in gray cartoon, amino acid positions that stabilize enzyme are in red stick, tunnel is in gold surface.

Type II cholesterol oxidase BsChOx from *Brevibacterium sterolicum* catalyzes the oxidation of steroid substrates which have a hydroxyl group at the 3β position of the steroid ring system. Molecular tunnel that is proposed to serve in the access of dioxygen to the active site is approximately 23 Å long. List of selected mutations with predicted ΔΔG and standard deviation of different run results are presented in Table 5. Selected residues and the access tunnel are visualized in FIG. 7.

TABLE 5

Predicted ΔΔG and standard deviation of different run results of selected tunnel mutants of type II cholesterol oxidase from *Brevibacterium sterolicum*.

| Residue | Position | Mutation | ΔΔG [kcal/mol] | SD |
|---|---|---|---|---|
| A | 205 | M | −1.84 | 0.22 |
| A | 205 | L | −1.72 | 0.07 |
| A | 205 | I | −0.87 | 0.20 |
| Q | 211 | F | −0.73 | 0.13 |
| Q | 211 | L | −0.65 | 0.04 |
| T | 212 | F | −1.12 | 0.02 |
| T | 212 | Y | −0.92 | 0.03 |
| T | 212 | P | −0.62 | 0.01 |
| L | 214 | W | −1.08 | 0.07 |
| L | 214 | P | −0.82 | 0.02 |
| L | 214 | M | −0.75 | 0.06 |
| Y | 219 | W | −1.38 | 0.08 |
| Y | 219 | F | −0.66 | 0.03 |
| Q | 276 | M | −1.74 | 0.19 |
| G | 309 | M | −1.57 | 0.06 |
| V | 328 | M | −0.64 | 0.06 |

Ni—Fe Hydrogenase.

Figure 8:
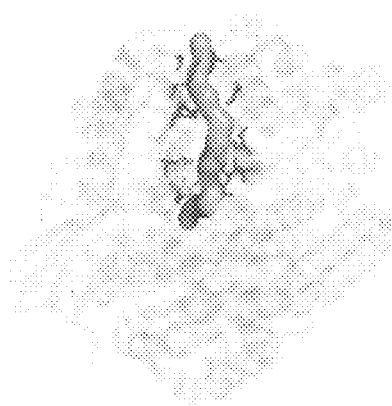
FIG. 8. Structure of Ni—Fe hydrogenase from *Desulfovibrio fructosovorans*. Overall enzyme structure is represented in gray cartoon, amino acid positions that stabilize enzyme are in red stick, tunnel is in gold surface.

Ni—Fe hydrogenase from *Desulfovibrio fructosovorans* catalyzes biological conversion between dihydrogen and protons. The dinuclear active site is connected to the solvent by a hydrophobic tunnel approximately 38 Å long. List of selected mutations with predicted ΔΔG and standard deviation of different run results are presented in Table 6. Selected residues and the tunnel are visualized in FIG. 8.

TABLE 6

Predicted ΔΔG and standard deviation of different run results of selected tunnel mutants of Ni—Fe hydrogenase from *Desulfovibrio fructosovorans*.

| Residue | Position | Mutation | ΔΔG [kcal/mol] | SD |
|---|---|---|---|---|
| V | 9 | F | −1.45 | 0.19 |
| V | 9 | I | −1.05 | 0.02 |
| V | 9 | M | −1.02 | 0.04 |
| V | 9 | L | −0.59 | 0.07 |
| E | 22 | W | −1.21 | 0.48 |
| E | 22 | M | −0.97 | 0.03 |
| I | 32 | W | −2.20 | 0.03 |
| I | 32 | F | −1.14 | 0.04 |
| I | 32 | P | −0.84 | 0.01 |
| L | 35 | F | −1.37 | 0.02 |
| Q | 45 | M | −1.36 | 0.15 |
| T | 47 | Y | −3.39 | 0.17 |
| T | 47 | F | −3.06 | 0.03 |
| T | 47 | W | −1.74 | 0.91 |
| T | 47 | M | −1.60 | 0.05 |
| T | 47 | L | −1.21 | 0.04 |
| T | 47 | I | −1.20 | 0.01 |
| I | 48 | Y | −1.41 | 0.05 |
| I | 48 | F | −1.24 | 0.04 |
| Y | 71 | M | −1.31 | 0.11 |
| Y | 71 | L | −1.03 | 0.10 |
| Y | 71 | W | −0.70 | 0.09 |
| V | 73 | I | −1.08 | 0.01 |
| V | 73 | M | −0.88 | 0.05 |
| G | 107 | Q | −2.24 | 0.45 |
| G | 107 | E | −2.23 | 0.10 |
| G | 107 | M | −1.96 | 0.14 |
| G | 107 | L | −1.82 | 0.52 |
| G | 107 | S | −1.69 | 0.02 |
| G | 107 | I | −1.55 | 0.39 |
| G | 107 | K | −1.49 | 0.59 |
| G | 107 | T | −1.49 | 0.01 |
| G | 107 | A | −1.38 | 0.01 |
| G | 107 | R | −1.36 | 0.33 |
| G | 107 | C | −1.32 | 0.11 |
| G | 107 | V | −0.90 | 0.13 |
| G | 107 | N | −0.81 | 0.05 |
| I | 142 | L | −0.62 | 0.02 |
| V | 158 | M | −1.60 | 0.08 |
| V | 158 | L | −1.54 | 0.01 |

Curcuminoid Synthase (Type III Polyketide Synthases).

Figure 9:
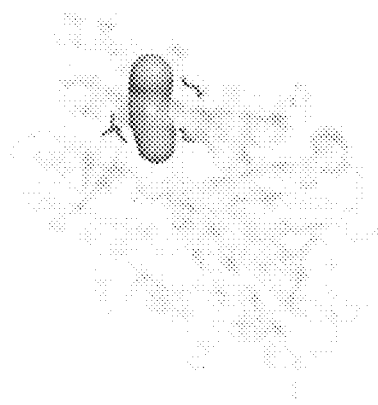
FIG. 9. Structure of curcuminoid synthase from *Oryza sativa*. Overall enzyme structure is represented in gray cartoon, amino acid positions that stabilize enzyme are in red stick, tunnel is in gold surface.

Curcuminoid synthase from *Oryza sativa* catalyzes the one-pot formation of the C(6)-C(7)-C(6) diarylheptanoid scaffold of bisdemethoxycurcumin, by the condensation of two molecules of 4-coumaroyl-CoA and one molecule of malonyl-CoA. Active site is located at the bottom of short 11 Å long tunnel. List of selected mutations with predicted ΔΔG and standard deviation of different run results are presented in Table 7. Selected residues and the tunnel are visualized in FIG. 9.

TABLE 7

Predicted ΔΔG and standard deviation of different run results of selected tunnel mutants of curcuminoid synthase from *Oryza sativa*.

| Residue | Position | Mutation | ΔΔG [kcal/mol] | SD |
|---|---|---|---|---|
| L | 276 | W | −0.68 | 0.03 |
| G | 318 | F | −3.76 | 0.20 |
| G | 318 | W | −3.44 | 0.28 |
| G | 318 | Y | −2.52 | 0.40 |
| G | 318 | L | −2.51 | 0.04 |
| G | 318 | M | −2.40 | 0.06 |
| G | 318 | I | −1.74 | 0.08 |
| G | 318 | E | −1.49 | 0.09 |
| G | 318 | P | −1.27 | 0.16 |
| G | 318 | V | −0.74 | 0.08 |
| G | 318 | Q | −0.72 | 0.18 |
| T | 321 | M | −1.34 | 0.19 |
| T | 321 | E | −0.99 | 0.02 |
| T | 321 | I | −0.86 | 0.02 |
| T | 321 | L | −0.86 | 0.08 |
| T | 321 | Q | −0.54 | 0.03 |

Acetylcholinesterase.

Figure 10:
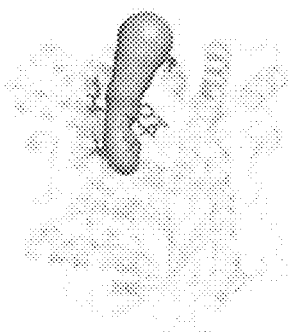
FIG. 10. Structure of acetylcholinesterase TcAChE from *Torpedo californica*. Overall enzyme structure is represented in gray cartoon, amino acid positions that stabilize enzyme are in red stick, tunnel is in gold surface.

Acetylcholinesterase TcAChE from *Torpedo californica* catalyzes hydrolysis of acetylcholine. The active site is connected with surface via approximately 24 Å long tunnel. List of selected mutations with predicted ΔΔG and standard deviation of different run results are presented in Table 8. Selected residues and the tunnel are visualized in FIG. 10.

TABLE 8

Predicted ΔΔG and standard deviation of different run results of selected tunnel mutants of acetylcholinesterase from *Torpedo californica*.

| Residue | Position | Mutation | ΔΔG [kcal/mol] | SD |
|---|---|---|---|---|
| Y | 70 | P | −0.73 | 0.05 |
| Q | 74 | M | −1.02 | 0.16 |
| Q | 74 | F | −0.88 | 0.11 |
| Q | 74 | L | −0.65 | 0.05 |
| Q | 74 | K | −0.61 | 0.03 |
| Q | 74 | Y | −0.59 | 0.03 |
| N | 280 | R | −0.76 | 0.08 |
| S | 286 | C | −1.12 | 0.01 |
| G | 335 | M | −1.89 | 0.06 |
| G | 335 | W | −1.57 | 0.08 |
| G | 335 | R | −1.24 | 0.06 |
| G | 335 | L | −1.23 | 0.03 |
| G | 335 | K | −1.11 | 0.05 |
| G | 335 | F | −1.10 | 0.04 |
| G | 335 | Y | −1.10 | 0.02 |
| G | 335 | Q | −1.05 | 0.02 |
| G | 335 | D | −0.66 | 0.06 |

Epoxide Hydrolase.

Figure 11:
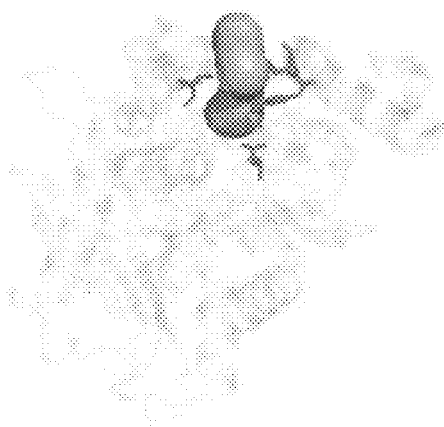
FIG. 11. Structure of epoxide hydrolases from *Aspergillus niger*. Overall enzyme structure represented in gray cartoon, amino acid positions that stabilize enzyme in red stick, tunnel in gold surface.

Epoxide hydrolases from *Aspergillus niger* converts epoxides into less toxic diols. The active site is connected with surface via approximately 18 Å long tunnel. List of selected mutations with predicted ΔΔG and standard deviation of different run results are presented in Table 9. Selected residues and the tunnel are visualized in FIG. 11.

TABLE 9

Predicted ΔΔG and standard deviation of different run results of selected tunnel mutants of epoxide hydrolases from *Aspergillus niger*.

| Residue | Position | Mutaion | ΔΔG [kcal/mol] | SD |
|---|---|---|---|---|
| L | 215 | F | −1.43 | 0.06 |
| L | 215 | Y | −0.68 | 0.06 |
| A | 217 | M | −2.53 | 0.13 |
| A | 217 | P | −2.04 | 0.01 |

TABLE 9-continued

Predicted ΔΔG and standard deviation of different run results of selected tunnel mutants of epoxide hydrolases from *Aspergillus niger*.

| Residue | Position | Mutaion | ΔΔG [kcal/mol] | SD |
|---|---|---|---|---|
| A | 217 | I | −1.64 | 0.01 |
| A | 217 | L | −1.57 | 0.03 |
| A | 217 | V | −0.96 | 0.04 |
| A | 217 | Q | −0.65 | 0.05 |
| A | 217 | C | −0.61 | 0.02 |
| F | 244 | Y | −0.64 | 0.02 |
| M | 245 | F | −0.80 | 0.05 |
| T | 317 | M | −1.61 | 0.29 |
| T | 317 | I | −1.20 | 0.02 |
| T | 317 | V | −0.71 | 0.03 |

Conclusions

A computational tool was applied to design stabilizing mutations in six randomly selected proteins with buried active sites, very different protein folds and catalyzing diverse chemical reactions. Six studied proteins contained 12-34 residues lining the access tunnels, while excluding the residues located at the protein exterior and forming the active site. Out of these, 3-12 could be stabilized by 14-40 different substitutions, providing up to 3.7 kcal/mol stabilization per substitution. Proposed substitutions can be easily introduced by site-directed mutagenesis. Alternatively, permutations can be made in selected positions by directed evolution, followed by biochemical screening or selection. These results confirm wide applicability of the concept of tunnel engineering for stabilization of proteins with buried active sites irrespective of protein fold or reaction mechanism.

Example 4

Analysis of Compatibility Between the Access Tunnels and Organic Solvents Applicable for Design of Solvent-Resistant Catalysts Introduction The structure and activity of three representative haloalkane dehalogenases: (i) DbjA from *Bradyrhizobium japonicum* USDA110, (ii) DhaA from *Rhodococcus rhodochrous* NCIMB13064 and (iii) LinB from *Sphingobium japonicum* UT26, were analysed in the presence of various concentrations of fourteen water-miscible organic solvents. These three enzymes were used as models for detailed investigation of structure-function relationships in non-conventional media. Mechanisms that define the solvent-enzyme interaction at the molecular level were studied by activity screening, structural analysis, molecular modeling and steady-state kinetic. Here we show that organic solvents have an ability to penetrate the access tunnel and the active site of studied enzymes. The occupancy of solvents in these regions represents good parameter for prediction of organic solvent effects on biocatalysts efficiency and can be used for the design of proteins compatible with a selected organic solvent of interest.

Methods

Protein expression and purification. The His-tagged LinB, DhaA and DbjA were overexpressed in *Escherichia coli* BL21 cells using a previously described method (Nagata, Y., Hynková, K., Damborský, J., and Takagi, M. 1999: Construction and characterization of histidine-tagged haloalkane dehalogenase (LinB) of a new substrate class from a gamma-hexachlorocyclohexane-degrading bacterium, *Sphingomonas paucimobilis* UT26. Protein Expression and Purification 17, 299-304; Pavlova, M., Klvana, M., Prokop, Z., Chaloupkova, R., Banas, P., Otyepka, M., Wade, R. C., Tsuda, M., Nagata, Y., and Damborsky, J. 2009: Redesigning dehalogenase access tunnels as a strategy for degrading an anthropogenic substrate. Nature Chemical Biology 5: 727-733; Sato, Y., Monincova, M., Chaloupkova, R., Prokop, Z., Ohtsubo, Y., Minamisawa, K., Tsuda, M., Damborsky, J., and Nagata, Y. 2005: Characterization of haloalkane dehalogenases of a new structure and substrate specificity from Rhizobiaceae strains *Mesorhizobium loti* MAFF303099 and *Bradyrhizobium japonicum* USDA110. Applied and Environmental Microbiology 71: 4372-4379). Proteins were purified on Ni-NTA Superflow Cartridge (Qiagen). His-tagged enzymes were bound to the resin in the equilibrating buffer (20 mM potassium phosphate buffer, pH 7.5 containing 0.5 M sodium chloride and 10 mM imidazole), unbound and weakly bound proteins were washed out. His-tagged enzymes were eluted by the buffer containing 300 mM imidazole. The active fractions were pooled and dialyzed overnight against 50 mM potassium phosphate buffer (pH 7.5) and then stored at 4° C. Protein's concentration was determined by Bradford reagent (Sigma-Aldrich). Purity of purified proteins was checked by SDS-PAGE.

Activity Assay.

Haloalkane dehalogenase activity was assayed at 37° C. by a previously described method (Iwasaki, I., Utsumi, S., and Ozawa, T. 1952: New colorimetric determination of chloride using mercuric thiocyanate and ferric ion. Bulletin of the Chemical Society of Japan 25: 226-226). The released halide ions were analysed spectrophotometrically at 460 nm after a reaction with mercuric thiocyanate and ferric ammonium sulphate. The reaction mixture was composed of 100 mM glycine buffer (pH 8.6), 2 µl of substrate 1-iodohexane and appropriate amount of organic solvent. Solvent concentration was increased until the enzyme activity dropped below fifty per cent. The reaction was initiated by the addition of enzyme in a final concentration of 0.15 µM. The reaction was monitored by withdrawing samples at periodical intervals from the reaction mixture. The samples were immediately mixed with 35% nitric acid to terminate the reaction. Dehalogenation activity was quantified as a rate of product formation in time. Each activity was measured in 3-5 independent replicates and expressed as mean values of relative activity, represented percentage of activity in pure buffer.

CD Spectroscopy.

Circular dichroism (CD) spectra of enzymes were performed at 37° C. using a Jasco J-810 spectropolarimeter equipped with a Peltier thermostat (Jasco). Data were collected from 185 to 260 nm, at 100 nm/min, 1 s response time and 2 nm bandwidth. Spectra were recorded in a 0.1-cm quartz cuvette containing 0.25 mg/ml enzyme in 50 mM phosphate buffer (pH 7.5) and defined amount of organic solvent. Each spectrum shown is the average of 10 scans and baseline corrected. CD spectra were expressed in terms of millidegrees (instrument units of CD). The comparison of CD spectra measured in buffer alone and in buffer/organic solvent systems was made by root mean square deviation (RMSD). The RMSD between CD spectra of enzymes exposed to the organic solvent and the spectra of folded enzymes ($RMSD_s$) related to RMSD between the spectra of enzymes unfolded by guanidine hydrochloride (GuHCl) and the spectra of folded enzymes ($RMSD_u$) was calculated using the equation:

$$RMSD_s/RMSD_u = \sqrt{\frac{\sum_{i=1}^{n}(X_{s,i}-X_{ref,i})^2}{\sum_{i=1}^{n}(X_{u,i}-X_{ref,i})^2}}$$

where $X_s$, $X_u$ and $X_{ref}$ are the CD signals from 205 to 230 nm of the spectrum measured in the presence of organic solvent, the spectrum of protein denatured by treatment with GuHCl, and the reference spectrum in buffer, respectively.

Fluorescence Spectroscopy.

Intrinsic fluorescence emission spectra of enzymes were performed using a FluoroMax-4P (HORIBA Jobin Yvon, New Jersey, USA) spectrometer. Fluorescence data were collected from 270 to 450 nm with an excitation wavelength of 280 nm, at 50 nm/min and bandpasses set to 1 nm. Spectra were recorded in a 0.5-cm quartz cuvette containing 0.25 mg/ml enzyme in 50 mM phosphate buffer (pH 7.5) and defined amount of organic solvent. All samples were incubated at 37° C. for 10 min prior measurement. Each spectrum was baseline corrected and expressed in terms of arbitrary units (units of fluorometer). The comparison of the fluorescence spectra measured in buffer alone and in buffer/organic solvent systems was made by determination of the shift in emission maxima.

Molecular Dynamics Simulations.

Molecular dynamics simulations were conducted by M. Khabiri, B. Minofar and R. Ettrich (University South Bohemia, Czech Republic) using the modeling package GROMACS 3.3.3 (Lindahl, E., Hess, B., and van der Spoel, D. 2001: GROMACS 3.0: A package for molecular simulation and trajectory analysis. Journal of Molecular Modeling, 7: 306-317) with an extended All Atom Optimized Potentials for Liquid Simulation (OPLSAA) force field (Jorgensen, W. L, Maxwell, D. S, and Tirado-Rives, J. 1996: Development and testing of the OPLS all-atom force field on conformational energetics and properties of organic liquids. Journal of the American Chemical Society 118: 11225-11236) in the isothermal isobaric ensemble. Periodic boundary conditions were applied. Weak temperature and pressure coupling (Berendsen, H. J. C., Postma, J. P. M., van Gunsteren, W. F., Di Nola, A., and Haak, J. R. J. 1984: Molecular dynamics with coupling to an external bath, Chemical Physics 8: 3684-3690) were employed (coupling constants 0.1 ps), with the protein and solvent atoms having separate baths maintained at 300 K, and pressure maintained at 1 bar with a compressibility of 4.6*1025/bar. Electrostatics were evaluated using the particle-mesh Ewald method (Essmann, U., Perera, L., and Berkowitz, M. L. 1995: A smooth particle mesh Ewald method. Journal of Chemical Physics 103: 8577-859) with a direct interaction cut-off of 10 Å. Van der Waals forces were evaluated with a Lennard-Jones potential having an 10 Å cut-off. Covalent bond lengths were constrained by the linear constraint solver algorithm (Hess, B., Bekker, H., Berendsen, H. J. C., and Fraaije, J. G. 1997: LINCS: A Linear constraint solver for molecular simulations. Journal of Computational Chemistry 18: 1463-1742). Three different mixtures of organic solvents with extended simple point charge [formamide 5% (v/v), acetone 20% (v/v) and isopropanol 10% (v/v)] were prepared to correspond with the experimental conditions. Three-dimensional structures of the organic molecules were optimized and partial charges were calculated in Gaussian 03 employing the Hartree fock method and the 6-31G* basic set (Frisch, M. J. T., Schlegel, G. W., Scuseria, H. B., Robb, G. E., Cheeseman, M. A. et al. 2004: Gaussian 03, Gaussian, Inc., Wallingford Conn.). Geometries were optimized at mp2/6-31G level. Topologies for all organic molecules were generated using MKTOP (Ribeiro, A. A. S. T., Horta, B. A. C., and de Alencastro, R. B. 2008: MKTOP: A Program for automatic construction of molecular topologies. Journal of the Brazilian Chemical Society 19: 1433-1435) for the OPLSAA forcefield. Crystal structure coordinates for DhaA (PDB ID: 1CQW), DbjA (PDB ID: 3A2M) and LINB (PDB ID: 1MJ5) were downloaded from the Protein Data Bank. Three substitutions were introduced in silico to DhaA (V172A, I209L and G292A) to match the primary structure from *Rhodococcus rhodochrous* NCIMB13064. Crystallographic water molecules were kept in place. Protonable residues of all three enzymes were used as observed in water. Initially, crystal structures were energy minimized in vacuo by steepest descent minimization for at least 1000 steps. Minimized crystal structures were solvated in pre-equilibrated water (Berendsen, H. J. C., Grigera, J. R., and Straatsma, T. P. 1987: The missing term in effective pair potential. Journal of Physical Chemistry 91: 6269-6271), formamide 5%, isopropanol 10% and acetone 20% in a rectangular box with a minimum distance of 1.5 nm between the protein and box edges. Sodium counterions were added by replacing water molecules to provide a neutral simulation box. The solvated system was first energy minimized using steepest descent and the solvent was allowed to relax for 2 ns while keeping the protein restrained. Initial Maxwell-Boltzmann-weighted velocities were generated randomly and the system was further equilibrated by gradually heating from 290 to 300 K during 50 ps of simulation. All simulations were run for 35 ns.

Isothermal Titration Calorimetry.

Substrate to product conversion by the action of enzymes was carried out using VP-ITC isothermal titration microcalorimeter (MicroCal), by single injection method. The substrate 1-iodohexane was dissolved in 100 mM glycine buffer (pH 8.6) containing appropriate volume of organic solvent and equilibrated at 25° C. in the sample cell (1.4 ml). The reaction was initiated by injecting of 10 µl of 1 mg/ml enzyme solution dialyzed overnight against the same solution as used for dissolving of the substrate. The heat flow (µcal s$^{-1}$) was recorded as a function of time. The reaction rate was calculated according to the equation:

$$\frac{dQ}{dt} = -\Delta H V \frac{d[S]}{dt}$$

where V is the volume of the sample cell, [S] is substrate concentration and ΔH is the enthalpy of the conversion of substrate to product and was determined experimentally by titration of the substrate into the sample cell containing the enzyme. The evaluated rate of substrate depletion (−d[S]/dt), and corresponding substrate concentration were fitted by nonlinear regression to kinetic models by using Origin 6.1 software (OriginLab, Massachusetts, USA).

Results

Figure 12:
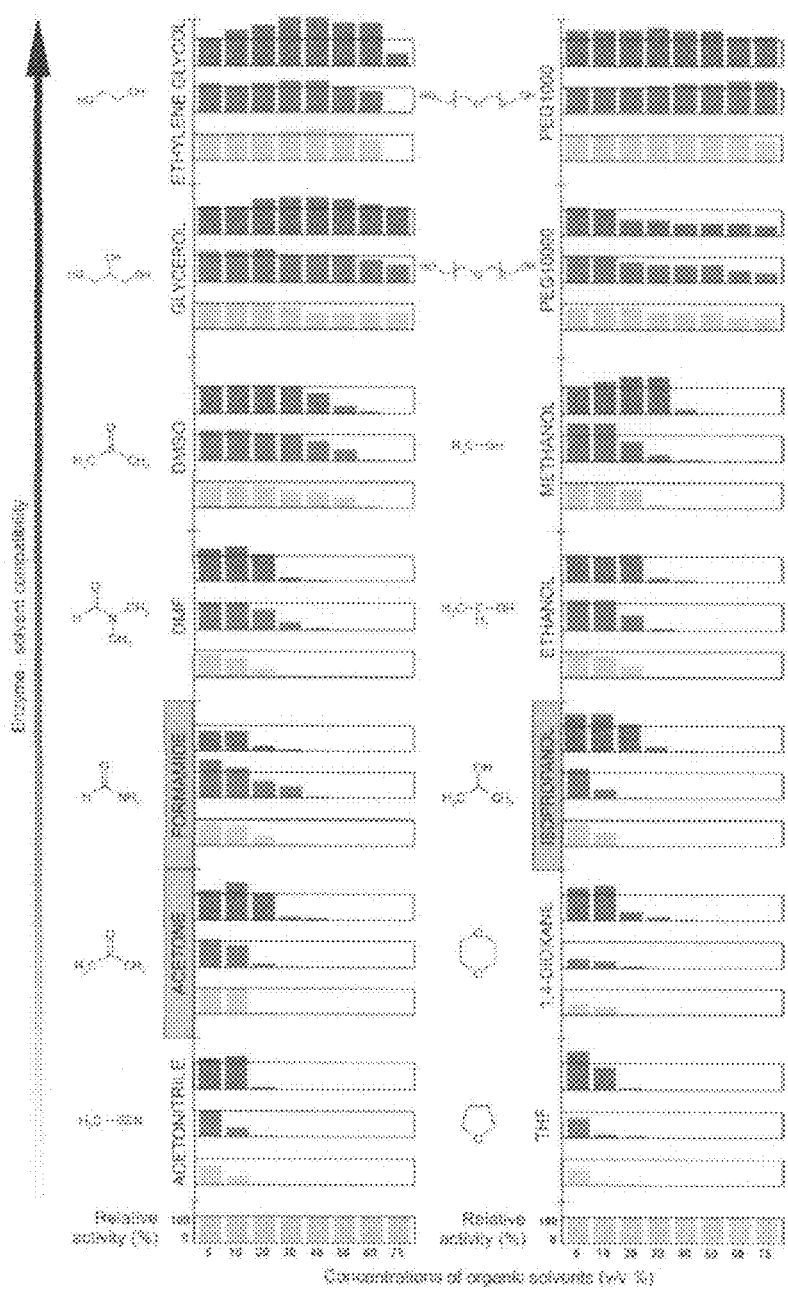
FIG. 12. The relative activities of DbjA (green), DhaA (blue) and LinB (yellow) in the presence of organic solvents. The activities are expressed as the percentage of specific activity in glycine buffer. Specific activities (in $\mu mol\ s^{-1}\ mg^{-1}$ of enzyme) of DbjA, DhaA and LinB in glycine buffer were 0.0213, 0.0355 and 0.0510, respectively.

The effects of various concentrations of fourteen water-miscible organic solvents on activity of three haloalkane dehalogenases DbjA, DhaA and LinB were investigated (FIG. 12). Studied enzymes exhibited different solvent-resistance, although they all belong to the same protein family.

Figure 13:
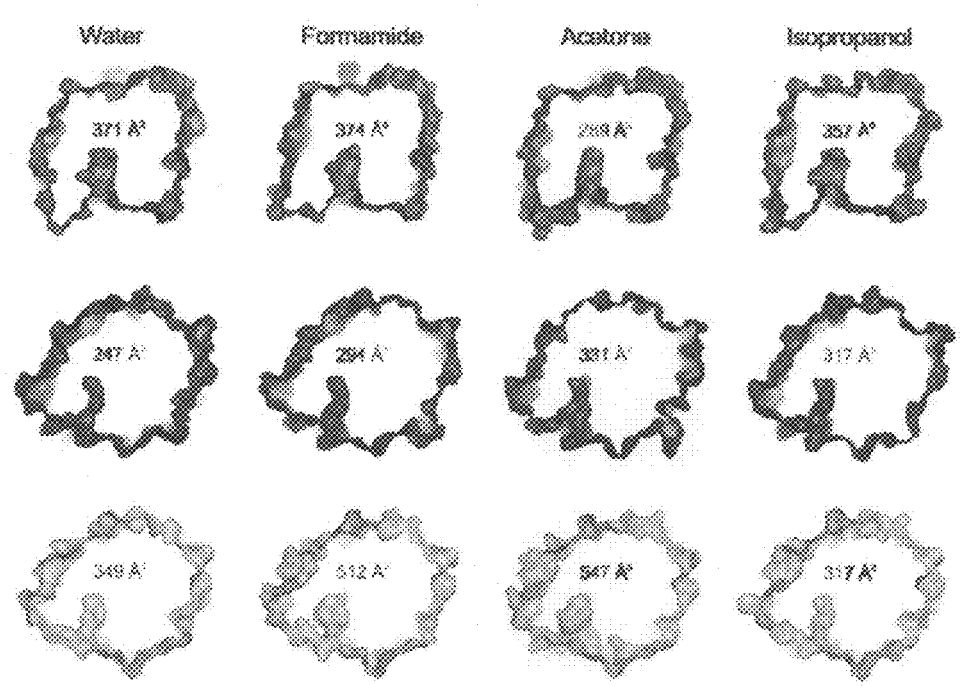
FIG. 13. Representative geometries of DbjA (green), DhaA (blue) and LinB (yellow) cavities obtained from MD simulation in water and in organic solvents. The values refer to the averaged volumes of calculated over 4000 snapshots.
Figure 14:
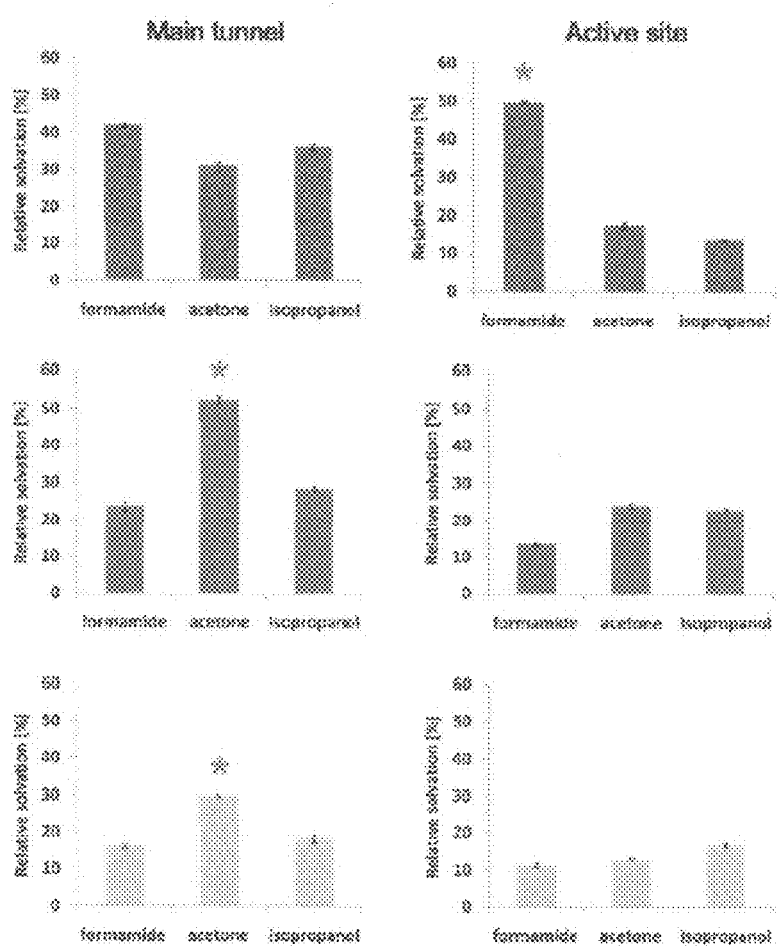
FIG. 14. Solvation of the main access tunnel and the active site of DbjA (green), DhaA (blue) and LinB (yellow) by solvent molecules. The conditions corresponding to experimentally observed drop in enzyme activity is indicated by the red stars. Relative solvation describes a ratio between volume of the main access tunnel or the active site occupied by solvent molecules and the total volume of the main tunnel and the active site.

Interactions between studied HLDs and the solvents formamide 5%, acetone 20% and isopropanol 10% were studied using molecular modelling. Selected solvents significantly altered activities of tested enzymes even at low non-denaturing concentrations. Although the effects of solvents on overall structure of HLDs are minimal, volumes and geometry of enzyme active sites and access tunnel in individual solvents differ significantly (FIG. 13). All solvents caused up to 2-fold expansion of DhaA main tunnel, while isopropanol also enlarged its active site. Similarly, the acetone and formamide expanded LinB tunnel by 2-fold and also slightly increased volume of its active site. On the contrary, isopropanol caused >10% reduction of LinB active site, while its main tunnel remained intact. In case of DbjA, only acetone had significant effect on the structure of active site and tunnel, reducing the volumes by 20% and 30%, respectively. All three solvents entered the access tunnels and the enzyme active sites and preferably remained inside the protein during 35 ns simulations. Two different mechanisms of solvent-induced haloalkane dehalogenase inhibition were identified. Firstly, the enzyme inactivation was observed when promotion of substrate inhibition exceeds improvement in substrate binding affinity to the free enzyme. Secondly, drop in enzyme activity was due to reduction of catalytic constant—the solvent molecules predominantly occupied the main tunnel leading to the enzyme active site, implying difficulty in either substrate entrance or product release (FIG. 14, Table 10).

Two mechanisms were recognized for solvent-induced enzyme activation, both connected with reactivity improvement (Table 10). Firstly, increase in enzyme activity was attributed to improvement in catalytic constant. Enhanced catalytic activity may be attributed to increased conformational flexibility of the enzyme by the polar organic solvent addition leading to the transition state stabilization (Toth, K., Sedlak, E., Musatov, A., and Zoldak, G. 2010: Activity of NADH oxidase from *Thermus thermophilus* in water/alcohol binary mixtures is limited by the stability of quaternary structure. Journal of Molecular Catalysis B: Enzymatic 64: 60-67; Verma, S. K., and Ghosh, K. K. 2010: Catalytic activity of enzyme in water/organic cosolvent mixtures for the hydrolysis of p-nitrophenyl acetate and p-nitrophenyl benzoate. Indian Journal of Chemistry 49A: 1041-1046). Increase in the catalytic constant was observed for DbjA in acetone and isopropanol and for DhaA in formamide. Secondly, the enzyme activation was caused by improvement in degree of substrate inhibition partiality which represents the higher productivity of the triple-substrate-enzyme complex. Partial substrate inhibition was distinguished in the kinetics of LinB towards 1-iodohexane and was not determined for other two enzymes. This phenomenon could be assigned to the narrow bottleneck present in the LinB access tunnel, compared to solvent accessible tunnels of DhaA and DbjA (Damborsky, J., Chaloupkova, R., Pavlova, M., Chovancova, E., Brezovsky, J. 2010: Microbiology of hydrocarbons, oils, lipids, and derived compounds, Springer-Verlag, Berlin; Prokop, Z., Sato, Y., Brezovsky, J., Mozga, T., Chaloupkova, R., Koudelakova, T., Jerabek, P., Stepankova, V., Natsume, R., van Leeuwen, J. G. E., Janssen, D. B., Florian, J., Nagata, Y., Senda, T., Damborsky, J. 2010: Enantioselectivity of haloalkane dehalogenases and its modulation by surface loop engineering. Angewandte Chemie International Edition 49: 6111-6115; Newman, J., Peat, T. S., Richard, R., Kan, L., Swanson, P. E., Affholter, J. A., Holmes, I. H., Schindler, J. F., Unkefer, C. J., and Terwilliger, T. C. 1999: Haloalkane dehalogenases: structure of a Rhodococcus enzyme. Biochemistry 38: 16105-16114; Marek, J., Vevodova, J., Smatanova, I. K., Nagata, Y., Svensson, L. A., Newman, J., Takagi, M., and Damborsky, J. 2000: Crystal structure of the haloalkane dehalogenase from *Sphingomonas paucimobilis* UT26. Biochemistry 39: 14082-14086). The LinB activation, connected with enhancement of substrate inhibition partiality, was observed in the presence of isopropanol. The molecules of isopropanol induced reduction of LinB active site and no extension of the main tunnel while the other solvents (formamide and acetone) caused its enlargement more than two-fold.

TABLE 10

Steady-state kinetic parameters of DbjA, DhaA and LinB for conversion of 1-iodohexane determined in glycine buffer, formamide 5% (v/v), acetone 20% (v/v) and isopropanol 10% (v/v)*,†.

| Enzyme | Reaction medium | $k_{cat}$, $s^{-1}$ | $K_{0.5}$, μM | $K_{si}$, mM | $n_H$ | b | $a_r$‡, % |
|---|---|---|---|---|---|---|---|
| DbjA | buffer | 1.1 | 8.0 | 1.6 | 2.0 | —§ | 100 |
|  | formamide | 1.2 | 5.9 | 0.3 | 1.9 | —§ | 82 |
|  | acetone | 1.7 | 5.0 | 18.4 | 1.7 | —§ | 123 |
|  | isopropanol | 1.6 | 2.9 | 0.6 | 2.0 | —§ | 118 |
| DhaA | buffer | 0.9 | 8.5 | 1.1 | 2.0 | —§ | 100 |
|  | formamide | 1.3 | 4.2 | 0.6 | 2.0 | —§ | 130 |
| LinB | buffer | 5.5 | 29.0 | 0.1 | 1.6 | 0.2 | 100 |
|  | acetone | 2.2 | 6.9 | —§ | —§ | —§ | 79 |
|  | isopropanol | 5.0 | 19.2o | 0.0 | 1.4 | 0.5 | 117 |

$k_{cat}$—catalytic constant,
$K_{0.5}$—concentration of substrate at half maximal velocity,
$K_{si}$—substrate inhibition constant,
$n_H$—Hill coefficient,
b—degree of partial inhibition,
$a_r$—relative activity,
*All measurements were performed at pH 8.6 and 25° C.,
†All parameters had standard errors of less than 10%,
‡The relative activities represented the percentage of specific activity in glycine buffer. Specific activities (in μmol $s^{-1}$ $mg^{-1}$ of enzyme) of DbjA, DhaA and LinB in glycine buffer were 0.0110, 0.0135 and 0.0180, respectively.
§not applicable Conclusions Variability in the enzyme efficiency is a consequence of: (i) conformational changes in protein structure, (ii) penetration of organic solvent molecules into the enzyme active site and the access tunnel and (iii) different occupancy of these regions by the solvent. These observations open up the possibility to predict enzyme behaviour in water-solvent mixtures, based on the correlation of enzyme performance with extent of access tunnel/active site occupancy by the solvent, and to engineer proteins resistant towards particular organic solvents by modification of the bottlenecks of their access tunnels.

The invention claimed is:

1. A method of thermo stabilization of a protein and/or stabilization of a protein towards organic solvents wherein the protein contains access routes, comprising the following steps:
    a) identification of amino acids forming the bottlenecks of the access routes, wherein said amino acids control the exchange of the solvent between the buried protein core and the surrounding environment and/or in the packing of the amino acids inside the access route;
    b) modification of the amino acids determined in the step a) so that the packing of the amino acids in the bottleneck of the tunnel is improved and the new anatomy of the bottleneck of the access route prevents the access of the undesired solvent molecules to the protein core, while it allows the passage of the molecules necessary for the protein to perform its biological function.

2. The method according to claim 1, further comprising a step of:
    c) assessment of the result of the modification, wherein the protein is analyzed in the form of whole cells containing the expressed protein, crude extract, or partially purified or purified protein.

3. The method according to claim 1, wherein in step b) the modification of the amino acids consists in replacing them by amino acids with aromatic side-chains.

4. The method according to claim 1, wherein the amino acids replacing in step b) the amino acids determined in step a) are determined by saturation mutagenesis using directed evolution techniques.

* * * * *